(12) United States Patent
Hammock et al.

(10) Patent No.: US 8,399,425 B2
(45) Date of Patent: *Mar. 19, 2013

(54) ALLEVIATING NEUROPATHIC PAIN WITH EETS AND SEH INHIBITORS

(75) Inventors: Bruce D. Hammock, Davis, CA (US); Ahmet Bora Inceoglu, Davis, CA (US); Steven L. Jinks, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 12/741,016

(22) PCT Filed: Nov. 7, 2008

(86) PCT No.: PCT/US2008/082853
§ 371 (c)(1), (2), (4) Date: Jun. 11, 2010

(87) PCT Pub. No.: WO2009/062073
PCT Pub. Date: May 14, 2009

(65) Prior Publication Data
US 2010/0267807 A1    Oct. 21, 2010

Related U.S. Application Data

(60) Provisional application No. 60/986,560, filed on Nov. 8, 2007.

(51) Int. Cl.
*A61K 31/7105* (2006.01)
*A61K 31/20* (2006.01)
*A61K 31/195* (2006.01)
*A61K 31/215* (2006.01)
*A61K 31/17* (2006.01)
*A61K 31/445* (2006.01)

(52) U.S. Cl. .......... 514/44; 514/560; 514/564; 514/529; 514/588; 514/331

(58) Field of Classification Search .................... 514/44, 514/560, 564, 529, 588, 331
See application file for complete search history.

(56) References Cited

U.S. PATENT DOCUMENTS
2004/0038917 A1   2/2004   Orntoft et al.
2006/0178347 A1   8/2006   Hammock et al.

FOREIGN PATENT DOCUMENTS
WO    WO 99/54282         10/1999
WO    WO 2006/086108      8/2006
WO    WO 2007/022509 A2   2/2007
WO    WO 2007/106525      9/2007
WO    WO 2008/016884      2/2008
WO    WO 2009/062073      5/2009

OTHER PUBLICATIONS

Boulton (Clinical Diabetes 23 (2005); 9-15).*
Rathmel et al. (Anesth. Analg (2005); 101:S30-43).*
Ahlgren et al, "Mechanical Hyperalgesia in Streptozotocin-Diabetic Rats", *Neuroscience*, vol. 52, No. 4, pp. 1049-1055, 1993.
Aley et al., "Rapid Onset Pain Induced by Intravenous Streptozotocin in the Rat", The Journal of Pain, vol. 2., No. 3 Jun. 2001: pp. 146-150.
Arnér et al., "Lack of analgesic effect of opioids on neuropathic and idiopathic forms of pain", Pain, 33 (1988) 11-23.
Basbaum, Allan I. et al., "Cellular and Molecular Mechanisms of Pain", Cell 139, Oct. 16, 2009, 267.
Basbaum, Allan I. et al., "Pain" Current Biology, vol. 9 No. 12, (1999).
Courteix et al., "Study of the sensitivity of the diabetes-induced pain model in rats to a range of analgesics", Pain, 57 (1994) 153-160.
Dworkin, Robert H. et al. "Pharmacologic management of neuropathic pain: Evidence-based recommendations", Pain 132 (2007) 237-251.
Inceoglu, Bora et al., "Inhibition of soluble epoxide hydrolase reduces LPS-induced thermal hyperalgesia and mechanical allodynia in a rat model of inflammatory pain", ScienceDirect, Life Sciences 79 (2006) 2311-2319.
Inceoglu, Bora et al., "Soluble epoxide hydrolase and epoxyeicosatrienoic acids modulate two distinct analgesic pathways", *Proc Natl Acad Sci USA*, Dec. 2, 2008, vol. 105, No. 48, 18901-18906.
Inceoglu, Bora et al., "Soluble epoxide hydrolase inhibition reveals novel biological functions of epoxyeicosatrienoic acids (EETs)", *Prostaglandins Other Lipid Mediat*, Jan. 2007; 82 (1-4): 42-49.
Inceoglu, Bora et al., "Acute augmentation of epoxygenated fatty acid levels rapidly reduces pain-related behavior in a rat model of type I diabetes", *Proc Natl Acad Sci USA*, Jun. 25, 2012, 109(28):11390-5.
Julius, David et al., "Molecular mechanisms of nociception", Nature, vol. 413, Sep. 13, 2001.
Kloke, et al., "Anti-depressants and anti-convulsants for the treatment of neuropathic pain syndromes in cancer patients," *Onkologie* (1991) 14(1):40-3.
Liu, Jun-Yan et al., "Inhibition of soluble epoxide hydrolase enhances the anti-inflammatory effects of aspirin and 5-lipoxygenase activation protein inhibitor in a murine model", Biochemical Pharmacology, 79 (2010) 880-887.
Melinkova, Irena, "Pain Market", Nature Reviews, vol. 9, Aug. 2010, 589.
Presley, et al., "Novel Approaches to the Treatment of Neuropathic Pain" West J Med (1992) 157(5):564.
Schmelzer et al., "Enhancement of anitnociception by coadministration of nonsterioidal anti-inflammatory drugs and soluble epoxide hydrolase inhibitors", *Proc Natl Acad Sci USA*, Sep. 12, 2006, vol. 103, No. 37, 13646-13651.
Snider, William D. et al., "Tackling Pain at the Source: New Ideas about Nociceptors", Neuron, vol. 20, 629-632, Apr. 1998.

(Continued)

*Primary Examiner* — Shirley V Gembeh
(74) *Attorney, Agent, or Firm* — Jennifer L. Wahlsten; Weaver Austin Villeneuve & Sampson LLP

(57) ABSTRACT

The invention discloses methods of using cis-epoxyeicosantrienoic acids ("EETs"), inhibitors of soluble epoxide hydrolase ("sEH"), or a combination of an EET and an inhibitor of sEH, to alleviate neuropathic pain in subjects suffering from such pain.

15 Claims, 5 Drawing Sheets

OTHER PUBLICATIONS

Xu, Qinghao et al., "A brief comparison of the pathophysiology of inflammatory versus neuropathic pain", *Current Opinion in Anesthesiology* 2011, 24:400-407.

International Search Report and Written Opinion dated Mar. 3, 2009 issued in PCT/US2008/082853 (WO/2009/062073).

International Preliminary Report on Patentability and Written Opinion dated May 11, 2010 issued in PCT/US2008/082853 (WO/2009/062073).

EP Extended Search Report dated Dec. 27, 2011 issued in EP08847164.4.

\* cited by examiner

SEQUENCE LISTING

```
<160> NUMBER OF SEQ ID NOS: 38

<210> SEQ ID NO 1

<400> SEQUENCE: 1

000

<210> SEQ ID NO 2

<400> SEQUENCE: 2

000

<210> SEQ ID NO 3
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      target sequence

<400> SEQUENCE: 3
cagtgttcat tggccatgac tgg                                              23

<210> SEQ ID NO 4
<211> LENGTH: 21
<212> TYPE: DNA
<213> ORGANISM: Artificial Sequence
<220> FEATURE:
<223> OTHER INFORMATION: synthetic soluble epoxide hydrolase (sEH) sense
      siRNA
<220> FEATURE:
<223> OTHER INFORMATION: Description of Combined synthetic DNA/RNA
      Molecule:soluble epoxide hydrolase (sEH) sense siRNA

<400> SEQUENCE: 4
guguucauug gccaugacut t                                                21

<210> SEQ ID NO 5
<211> LENGTH: 21
<212> TYPE: DNA
<213> ORGANISM: Artificial Sequence
<220> FEATURE:
<223> OTHER INFORMATION: ssynthetic oluble epoxide hydrolase (sEH)
      antisense siRNA
<220> FEATURE:
```

```
<223> OTHER INFORMATION: Description of Combined synthetic DNA/RNA
      Molecule:soluble epoxide hydrolase (sEH) antisense siRNA

<400> SEQUENCE: 5
agucauggcc aaugaacact t                                              21

<210> SEQ ID NO 6
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      target sequence

<400> SEQUENCE: 6
gaaaggctat ggagagtcat ctg                                            23

<210> SEQ ID NO 7
<211> LENGTH: 21
<212> TYPE: DNA
<213> ORGANISM: Artificial Sequence
<220> FEATURE:
<223> OTHER INFORMATION: synthetic soluble epoxide hydrolase (sEH) sense
      siRNA
<220> FEATURE:
<223> OTHER INFORMATION: Description of Combined synthetic DNA/RNA
      Molecule:soluble epoxide hydrolase (sEH) sense siRNA

<400> SEQUENCE: 7
aaggcuaugg agagucauct t                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic soluble epoxide hydrolase (sEH)
      antisense siRNA
<220> FEATURE:
<223> OTHER INFORMATION: Description of Combined synthetic DNA/RNA
      Molecule:soluble epoxide hydrolase (sEH) antisense siRNA

<400> SEQUENCE: 8
gaugacucuc cauagccuut t                                              21

<210> SEQ ID NO 9
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      target sequence

<400> SEQUENCE: 9
aaaggctatg gagagtcatc tgc                                            23

<210> SEQ ID NO 10
<211> LENGTH: 21
<212> TYPE: DNA
<213> ORGANISM: Artificial Sequence
<220> FEATURE:
<223> OTHER INFORMATION: soluble epoxide hydrolase (sEH) sense siRNA
<220> FEATURE:
<223> OTHER INFORMATION: Description of Combined synthetic DNA/RNA
      Molecule:soluble epoxide hydrolase (sEH) sense siRNA

<400> SEQUENCE: 10
aggcuaugga gagucaucut t                                              21
```

<210> SEQ ID NO 11
<211> LENGTH: 21
<212> TYPE: DNA
<213> ORGANISM: Artificial Sequence
<220> FEATURE:
<223> OTHER INFORMATION: synthetic soluble epoxide hydrolase (sEH)
      antisense siRNA
<220> FEATURE:
<223> OTHER INFORMATION: Description of Combined synthetic DNA/RNA
      Molecule:soluble epoxide hydrolase (sEH) antisense siRNA

<400> SEQUENCE: 11
agaugacucu ccauagccut t                                           21

<210> SEQ ID NO 12
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      target sequence

<400> SEQUENCE: 12
caagcagtgt tcattggcca tga                                         23

<210> SEQ ID NO 13
<211> LENGTH: 21
<212> TYPE: DNA
<213> ORGANISM: Artificial Sequence
<220> FEATURE:
<223> OTHER INFORMATION: synthetic soluble epoxide hydrolase (sEH) sense
      siRNA
<220> FEATURE:
<223> OTHER INFORMATION: Description of Combined synthetic DNA/RNA
      Molecule:soluble epoxide hydrolase (sEH) sense siRNA

<400> SEQUENCE: 13
agcaguguuc auuggccaut t                                           21

<210> SEQ ID NO 14
<211> LENGTH: 21
<212> TYPE: DNA
<213> ORGANISM: Artificial Sequence
<220> FEATURE:
<223> OTHER INFORMATION: synthetic soluble epoxide hydrolase (sEH)
      antisense siRNA
<220> FEATURE:
<223> OTHER INFORMATION: Description of Combined synthetic DNA/RNA
      Molecule:soluble epoxide hydrolase (sEH) antisense siRNA

<400> SEQUENCE: 14
auggccaaug aacacugcut t                                           21

<210> SEQ ID NO 15
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      target sequence

<400> SEQUENCE: 15
cagcacatgg aggactggat tcc                                         23

<210> SEQ ID NO 16
<211> LENGTH: 21
<212> TYPE: DNA
<213> ORGANISM: Artificial Sequence
<220> FEATURE:

```
<223> OTHER INFORMATION: synthetic soluble epoxide hydrolase (sEH) sense
      siRNA
<220> FEATURE:
<223> OTHER INFORMATION: Description of Combined synthetic DNA/RNA
      Molecule:soluble epoxide hydrolase (sEH) sense siRNA

<400> SEQUENCE: 16
gcacauggag acuggauut t                                              21

<210> SEQ ID NO 17
<211> LENGTH: 21
<212> TYPE: DNA
<213> ORGANISM: Artificial Sequence
<220> FEATURE:
<223> OTHER INFORMATION: synthetic soluble epoxide hydrolase (sEH)
      antisense siRNA
<220> FEATURE:
<223> OTHER INFORMATION: Description of Combined synthetic DNA/RNA
      Molecule:soluble epoxide hydrolase (sEH) antisense siRNA

<400> SEQUENCE: 17
aauccagucc uccaugugct t                                             21

<210> SEQ ID NO 18
<211> LENGTH: 9
<212> TYPE: DNA
<213> ORGANISM: Artificial Sequence
<220> FEATURE:
<223> OTHER INFORMATION: synthetic hairpin siRNA linker, short spacer

<400> SEQUENCE: 18 ttcaagaga                                                            9

<210> SEQ ID NO 19
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      hairpin siRNA target sequence

<400> SEQUENCE: 19
cagtgttcat tggccatgac tgg                                           23

<210> SEQ ID NO 20
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA sense strand

<400> SEQUENCE: 20
gatccccgtg ttcattggcc atgactttca agagaagtca tggccaatga acactttt     59

<210> SEQ ID NO 21
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA antisense strand

<400> SEQUENCE: 21
agctaaaaag tgttcattgg ccatgacttc tcttgaaagt catggccaat gaacacggg    59

<210> SEQ ID NO 22
<211> LENGTH: 23
```

```
<212> TYPE: DNA
<213> ORGANISM: Artificial Sequence
<220> FEATURE:
<223> OTHER INFORMATION: synthetic soluble epoxide hydrolase (sEH)
      hairpin siRNA target sequence

<400> SEQUENCE: 22
gaaaggctat ggagagtcat ctg                                         23

<210> SEQ ID NO 23
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA sense strand

<400> SEQUENCE: 23
gatccccaag gctatggaga gtcatcttca agagagatga ctctccatag ccttttttt    59

<210> SEQ ID NO 24
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA antisense strand

<400> SEQUENCE: 24
agctaaaaaa aggctatgga gagtcatctc tcttgaagat gactctccat agccttggg    59

<210> SEQ ID NO 25
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      hairpin siRNA target sequence

<400> SEQUENCE: 25
aaaggctatg gagagtcatc tgc                                         23

<210> SEQ ID NO 26
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA sense strand

<400> SEQUENCE: 26
gatccccagg ctatggagag tcatctttca agagaagatg actctccata gccttttt     59

<210> SEQ ID NO 27
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA antisense strand

<400> SEQUENCE: 27
agctaaaaaa ggctatggag agtcatcatc tcttgaaaga tgactctcca tagcctggg    59

<210> SEQ ID NO 28
<211> LENGTH: 23
<212> TYPE: DNA
<213> ORGANISM: Artificial Sequence
```

```
<220> FEATURE:
<223> OTHER INFORMATION: synthetic soluble epoxide hydrolase (sEH)
      hairpin siRNA target sequence

<400> SEQUENCE: 28
caagcagtgt tcattggcca tga                                          23

<210> SEQ ID NO 29
<211> LENGTH: 59
<212> TYPE: DNA
<213> ORGANISM: Artificial Sequence
<220> FEATURE:
<223> OTHER INFORMATION: soluble epoxide hydrolase (sEH) hairpin siRNA
      sense strand

<400> SEQUENCE: 29
gatccccagc agtgttcatt ggccatttca agagaatggc caatgaacac tgctttttt    59

<210> SEQ ID NO 30
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA antisense strand

<400> SEQUENCE: 30
agctaaaaaa gcagtgttca ttggccattc tcttgaaatg gccaatgaac actgctggg    59

<210> SEQ ID NO 31
<211> LENGTH: 23
<212> TYPE: DNA
<213> ORGANISM: Artificial Sequence
<220> FEATURE:
<223> OTHER INFORMATION: synthetic soluble epoxide hydrolase (sEH)
      hairpin siRNA target sequence

<400> SEQUENCE: 31
cagcacatgg aggactggat tcc                                          23

<210> SEQ ID NO 32
<211> LENGTH: 59
<212> TYPE: DNA
<213> ORGANISM: Artificial Sequence
<220> FEATURE:
<223> OTHER INFORMATION: synthetic soluble epoxide hydrolase (sEH)
      hairpin siRNA sense strand

<400> SEQUENCE: 32
gatccccgca catggaggac tggattttca agagaaatcc agtcctccat gtgctttttt   59

<210> SEQ ID NO 33
<211> LENGTH: 59
<212> TYPE: DNA
<213> ORGANISM: Artificial Sequence
<220> FEATURE:
<223> OTHER INFORMATION: soluble epoxide hydrolase (sEH) hairpin siRNA
      antisense strand

<400> SEQUENCE: 33
agctaaaaag cacatggagg actggatttc tcttgaaaat ccagtcctcc atgtgcggg    59

<210> SEQ ID NO 34
<211> LENGTH: 20
<212> TYPE: RNA
<213> ORGANISM: Artificial Sequence
<220> FEATURE:
<223> OTHER INFORMATION: synthetic soluble epoxide hydrolase (sEH)
```

```
                            -continued
        antisense sequence

<400> SEQUENCE: 34
uguccagugc ccacaguccu                                                 20

<210> SEQ ID NO 35
<211> LENGTH: 20
<212> TYPE: RNA
<213> ORGANISM: Artificial Sequence
<220> FEATURE:
<223> OTHER INFORMATION: soluble epoxide hydrolase (sEH) antisense
        sequence

<400> SEQUENCE: 35
uucccaccug acacgacucu                                                 20

<210> SEQ ID NO 36
<211> LENGTH: 20
<212> TYPE: RNA
<213> ORGANISM: Artificial Sequence
<220> FEATURE:
<223> OTHER INFORMATION: synthetic soluble epoxide hydrolase (sEH)
        antisense sequence

<400> SEQUENCE: 36
guucagccuc agccacuccu                                                 20

<210> SEQ ID NO 37
<211> LENGTH: 19
<212> TYPE: RNA
<213> ORGANISM: Artificial Sequence
<220> FEATURE:
<223> OTHER INFORMATION: synthetic soluble epoxide hydrolase (sEH)
        antisense sequence

<400> SEQUENCE: 37
aguccucccg cuucacaga                                                  19

<210> SEQ ID NO 38
<211> LENGTH: 21
<212> TYPE: RNA
<213> ORGANISM: Artificial Sequence
<220> FEATURE:
<223> OTHER INFORMATION: synthetic soluble epoxide hydrolase (sEH)
        antisense sequence

<400> SEQUENCE: 38
gcccacuucc aguuccuuuc c                                               21
```

ALLEVIATING NEUROPATHIC PAIN WITH EETS AND SEH INHIBITORS

CROSS-REFERENCES TO RELATED APPLICATIONS

This application is the U.S. National Stage entry under §371 of International Application No. PCT/US2008/082853, filed Nov. 7, 2008, which claims the benefit of U.S. Provisional Application No. 60/986,560, filed on Nov. 8, 2007, the entire disclosure of each is hereby incorporated herein by reference for all purposes.

STATEMENT AS TO RIGHTS TO INVENTIONS MADE UNDER FEDERALLY SPONSORED RESEARCH AND DEVELOPMENT

This invention was made with government support under Grant No. ES 002710, awarded by the National Institutes of Health. The United States government has certain rights in the invention.

BACKGROUND OF THE INVENTION

Pain is generally divided into nociceptive and neuropathic pain. Nociceptive pain stems from neural pathways in response to tissue damaging or potentially tissue damaging signals, and includes inflammatory pain. Neuropathic pain tends to relate to dysfunctions within the nervous system. Unfortunately, agents that treat one kind, of pain do not necessarily treat the other. Anti-inflammatory agents, for example, do not relieve the "phantom limb" pain felt by amputees.

In mammals, inflammatory pain is driven primarily by arachidonic acid (sometimes abbreviated, as "AA"). Inflammatory pain develops as a result of tissue injury such as a cut or a bacterial infection upon which a large amount of AA is released at the site of inure by the actions of phospholipases. Synchronized to this event is the upregulation of cyclooxygenase-2 (COX-2), an enzyme which converts the released AA to prostaglandins, potent pain producing molecules. Released AA is metabolized by cyclooxygenases ("COX"), lipoxygenases ("LOX") and cytochrome P450 epoxygenases to yield prostaglandins, leukotrienes and epoxy-eicosatrienoic acids ("EETs") respectively. These materials may be further metabolized, for example they may be converted to bioactive amides and conjugates. Inflammatory pain is well correlated with the production of Cox-2 metabolites of AA, the prostaglandin series molecules. Consequently, a profound decrease in pain follows the inhibition of the inducible Cox-2, which is often attributed to the reduction of $PGE_2$, a key regulator.

In contrast, in neuropathic pain, there is little evidence am inflammatory process mediated by arachidonic acid, cyclooxegenases and prostaglandins. Neuropathic pain is caused by a lesion of the peripheral or central nervous system (or both) manifesting with sensory symptoms and signs. Underlying causes include infections, trauma, metabolic abnormalities, chemotherapy, surgery, irradiation, neurotoxins, inherited neurodegeneration, nerve compression and tumor infiltration. Mechanisms of neuropathic pain are described, for example, in Zhuo. *Molecular Pain* (2007) 3:14 Campbell and Meyer, *Neuron* (2006) 52(1):77-91 Dworkin, et al., *Arch Neurol* (2.003) 60:1524-34.

The pharmacological agents that have most commonly been shown to effectively block neuropathic pain are tricyclic anti-depressants (TCAs). However these agents are not effective at all in some patients and are only partially effective in others. Therefore the therapy of neuropathic pain is an unmet and growing clinical need. TCAs have many disadvantages well known in the field. Since neuropathic pain is a debilitating and hard to treat condition, however. TCAs have been used despite their disadvantages in the absence of agents with less adverse effects.

BRIEF SUMMARY OF THE INVENTION

The present invention provides methods for treating, reducing, alleviating, inhibiting and/or preventing neuropathic pain by administration of a cis-epoxyeicosantrienoic acid ("EET"), an inhibitor of soluble epoxide hydrolase ("sEH"), and combinations thereof to a patient in need thereof.

Accordingly, in one aspect, the invention provides methods for relieving neuropathic pain in a subject in need thereof, said method comprising administering to said subject an effective amount of an agent or agents selected from the group consisting of a cis-epoxyeicosantrienoic acid ("EET"), an inhibitor of soluble epoxide hydrolase ("sEH"), and a combination of an EET and an inhibitor of sEH, thereby relieving said neuropathic pain in said subject.

In some embodiments, the agent is an EET. In some embodiments, the EET is selected from the group consisting of 14,15-EET, 8,9-EET, 11,12-EET or 5,6-EET. In some embodiments, the EET is synthetic or an EET analog.

In some embodiments, the agent is an inhibitor of sEH.

In some embodiments, the neuropathic pain is selected from the group consisting of post-herpetic neuralgia, trigeminal neuralgia, focal peripheral nerve injury, and anesthesia dolorosa, central pain due to stroke or mass lesion, spinal cord injury, or multiple sclerosis, and peripheral neuropathy due to diabetes. HIV, or chemotherapy.

In some embodiments, the neuropathic pain is chronic. In some embodiments, the subject is experiencing the neuropathic pain.

In some embodiments, the agent is administered orally. In some embodiments, the agent is administered intravenously. In some embodiments, the agent is administered intrathecally. In some embodiments, the agent is delivered directly to a damaged nerve.

In some embodiments, the neuropathic pain is central neuropathic pain, in some embodiments, the neuropathic pain is peripheral neuropathic pain.

In some embodiments, the subject or patient is a human.

DETAILED DESCRIPTION OF THE INVENTION'

Figure 1:
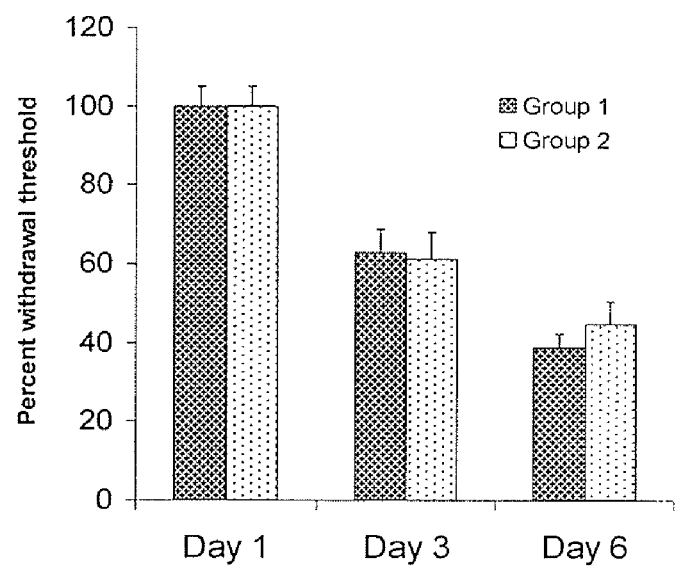
FIG. 1. Intravenous streptozocin administration (50 mg/kg) reduces the mechanical withdrawal threshold of rats.
Figure 2:
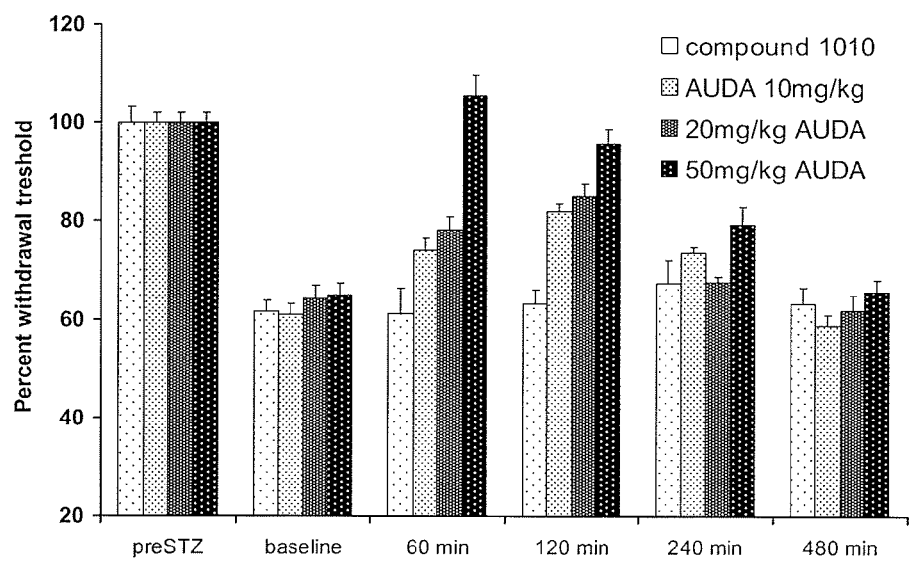
FIG. 2. shows the dose and time response relationship of three different doses of 12-(3-Adamantan-1-yl-ureido)dodecanoic acid ("AUDA") and one dose of compound 1010 in neuropathic rats, as determined using the von Frey test.
Figure 3:
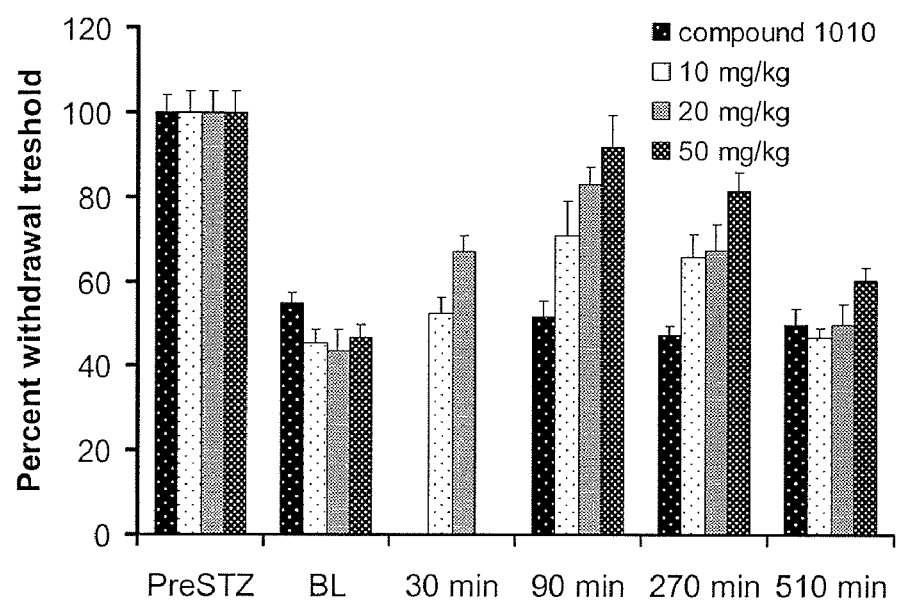
FIG. 3. shows that mechanical allodynia induced by diabetic neuropathy is reversed by an sEH inhibitor (e.g. AUDA) in a time and dose dependant manner. The inactive sEH inhibitor (e.g., compound 1010) however shows no effectiveness in reducing nociception in an equivalent dose. The first column, labeled "PreSTZ" is the normalized response of animals to the test before STZ administration. The second column, labeled "BL," (for "baseline") is the response of the animals to the test before the administration of sEHIs. Other columns reflect the results at the designated timepoints.
Figure 4:
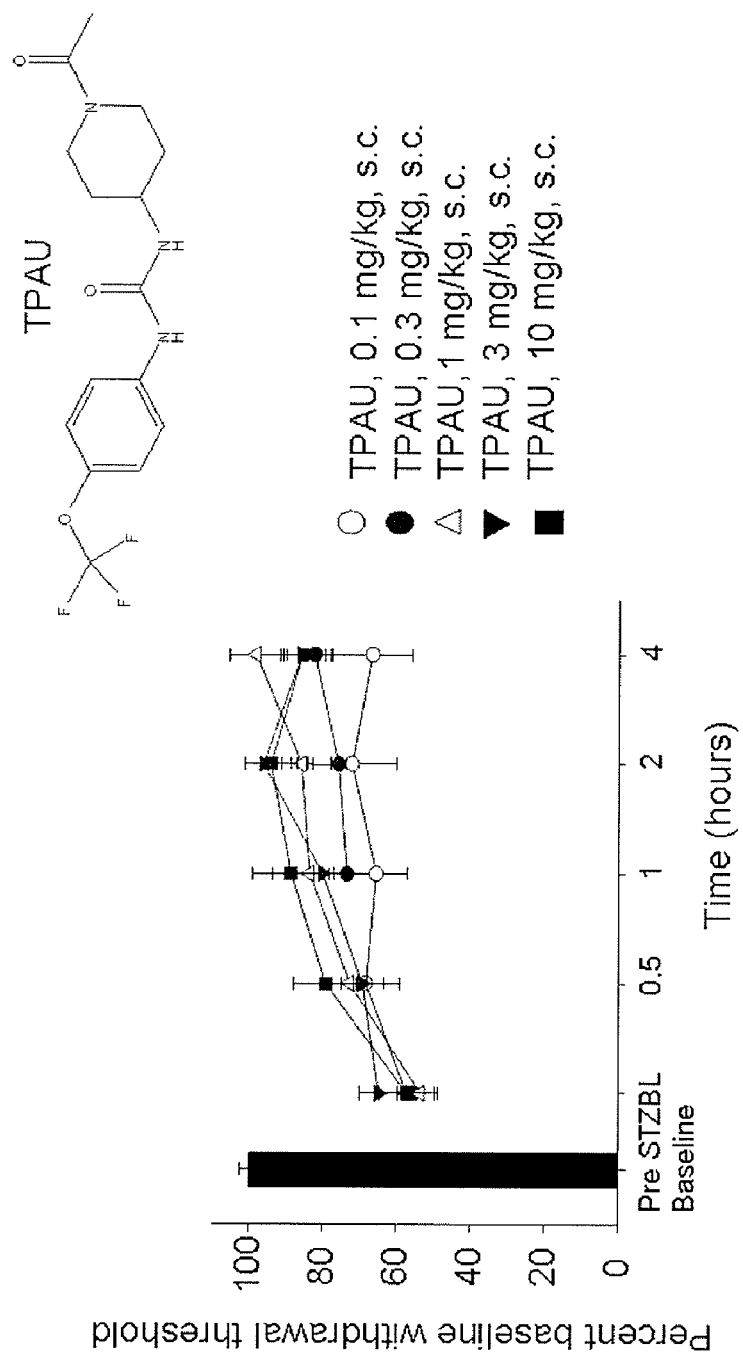
FIG. 4. shows the dose and time response relationship of five different doses of 1-trifluoromethoxyphenyl-3-(1-acetylpiperidin-4-yl) urea (also referred to herein as "TPAU") in neuropathic rats, as determined using the von Frey test.
Figure 5:
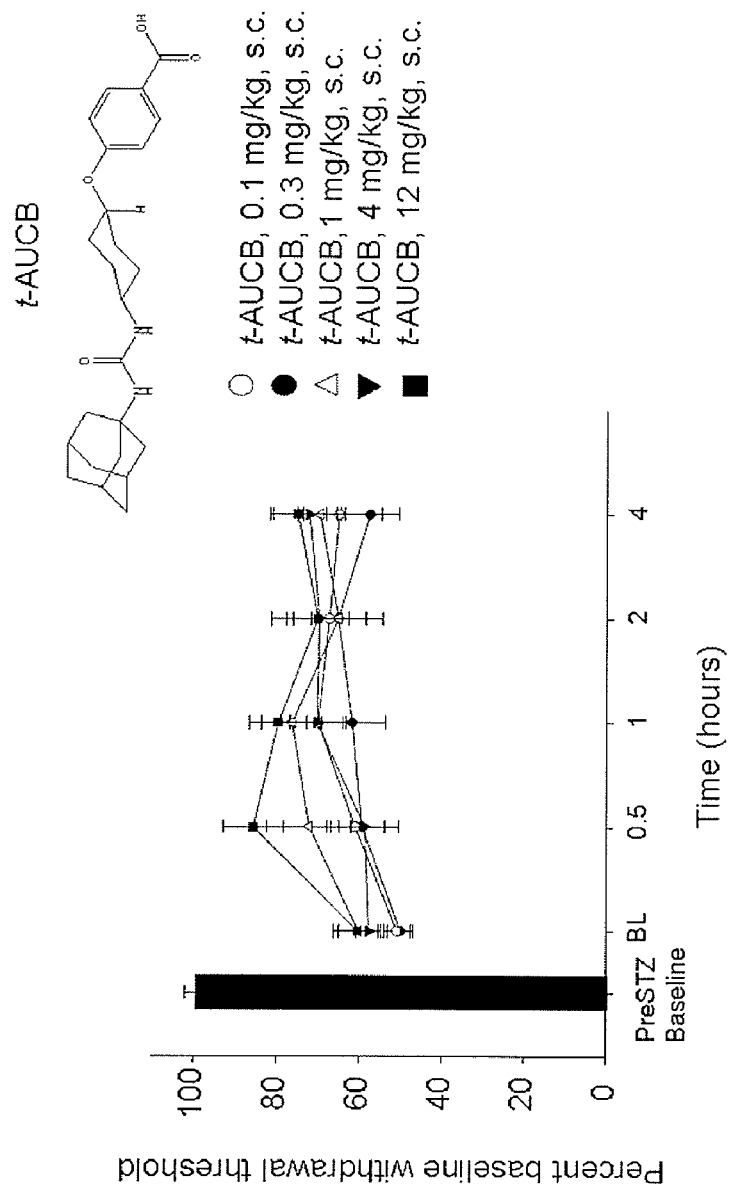
FIG. 5. shows the dose and time response relationship of five different doses of trans-4-[4-(3-adamantan-1-yl-ureido)-cyclohexyloxy]-benzoic acid (also referred to herein as "t-AUCB") in neuropathic rats, as determined using the von Frey test.

The enzyme "soluble epoxide hydrolase" ("sEH") acts on an important branch of the arachidonic acid pathway degrading anti-inflammatory and analgesic metabolites, cis-Epoxyeicosatrienoic acids" ("EETs") are biomediators synthesized by cytochrome P4.50 epoxygenases, and are hydrolyzed by sEH into the corresponding diols, which are pro-inflammatory. EETs and inhibitors of sEH, sometimes (the term "sEH inhibitors" is sometimes abbreviated herein as "sEHI") have been previously found to be useful as anti inflammatories.

Surprisingly, we have now found that sEHI and EETs are also useful to relieve neuropathic pain. Our discovery is the first example of a novel mechanism for pain control. We used a well-established method of quantifying pain in a well known model for neuropathic pain to elucidate the effects of inhibiting sEH and thus increasing the physiological concentration of EETs and/or other molecules containing epoxide functionality on pain perception. We demonstrated that sEH inhibitors surprisingly through a previously little known mechanism decrease the pain perception of treated animals that are suffering from neuropathic pain. Unknown and unexplored previously, inhibitors of sEH. EETs and/or polyunsaturated fatty acids like molecules containing epoxide functionality and precursors thereof such as 2-arachidonyglycerol ethanolamides of epoxy lipids and/or a combination thereof offer unique advantages as stand-alone therapeutic agents in treating, ameliorating, relieving, reducing, preventing and/or inhibiting neuropathic pain. We show that sEH inhibitors and EETs and/or polyunsaturated fatty acids containing epoxide functionality are analgesic and have a wide therapeutic efficacy in the treatment and management of neuropathic pain, including chronic neuropathic pain, including central and peripheral neuropathic pain. This is the first evidence that shows sEH inhibitors are effective in general for reducing neuropathic pain.

The model of neuropathic pain used is generally accepted as not involving inflammatory processes. This is because chemical and molecular analysis shows no upregulation of cyclooxygenases enzymes, and well known anti-inflammatory agents such as COX inhibitors are not effective in reducing neuropathic pain. Because sEH inhibitors were very effective in reducing inflammatory and nociceptive pain and because sEHIs decrease the release of key pain producing prostanoid PGE2, we hypothesized that sEH inhibitors would be ineffective in reducing neuropathic pain.

Neuropathy was induced by injecting animals with a bacterial toxin (streptozocin) that is known to kill the pancreatic beta cells, thus prevent the production of insulin, the key peptide regulating blood glucose levels. The result is that the animals have high plasma levels of glucose and become diabetic, with a concomitant neuropathic pain state. This neuropathy is unrelated to the inflammatory pain states that are driven by arachidonic acid release and production of prostaglandins and other inflammatory mediators. We then measured the pain thresholds of these animals before and after the induction of neuropathy using clinically relevant pain quantification methods and subsequently intervened with sEH inhibitors. As a control, we also used a metabolite of a potent sEH inhibitor. The metabolite, referred to as compound 1010, is structurally very similar to its parent compound, but is 250 fold less active in inhibiting sEH and is considered inactive. Compound 1010 was therefore used to determine whether any observed biological activity was due to activity in inhibiting sEH or to structural motifs or the like.

The structure of compound 1010, also referred to as "hydroxy-AEPU," is as follows:

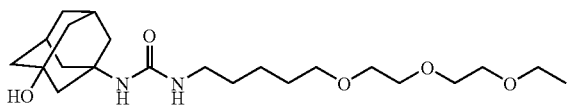 [SMILES: CCOCCOCCOCCCCCNC(=O)NC12CC3CC(CC(O)(C3)C1)C2]

Medicaments of EETs can be made which can be administered by themselves or in conjunction with one or more sEH inhibitors, or a medicament containing one or more sEH inhibitors can optionally contain one or more EETs. The EETs can be administered alone, concurrently with a sEH inhibitor or, or prior to or following administration of a sEH inhibitor. It is understood that, like all drugs, sEH inhibitors have half lives defined by the rate at which they are metabolized by or excreted from the body, and that the sEH inhibitor will have a period following administration during which it will be present in amounts sufficient to be effective. If EETs administered after an sEH inhibitor are intended to be administered while the sEH inhibition is still in effect, therefore, it is desirable that the EETs be administered during the period during which the inhibitor will be present in amounts to be effective to delay hydrolysis of the EETs. Typically, in such a situation, the EET or EETs will be administered within 48 hours of administering an sEH inhibitor. More preferably, where the effect of the EET or EETs is intended to be enhanced by the effect of an sEHI, the EET or EETs are administered within 24 hours of the inhibitor, and even more preferably within 12 hours. In increasing order of desirability, the EET or EETs are administered within 10, 8, 6, 4, 2, hours, 1 hour, or one half hour before or after administration of the sEH inhibitor. Most preferably, the EET or EETs are administered concurrently with the inhibitor.

In some embodiments, the person being treated with the EET or EETs is not being treated for atherosclerosis, other inflammatory conditions, or other conditions in which inhibition of adhesion molecule expression, particularly on endothelial cells, is desirable.

In some embodiments, the sEH inhibitor is an organic compound, for example, including the sEH inhibitors described herein and in U.S. Pat. Nos. 5,955,496; 6,150,415 and 6,531,506; U.S. Patent Publication No, 2005/0026844 and International Publication Nos. WO 2007/106525: WO 2006/045119; and WO 2004/089296, the disclosures of each of which are hereby incorporated by reference in their entirety for all purposes.

In some embodiments, the sEH inhibitor is an nucleic acid, such as a small interfering RNA (siRNA) or a micro RNA (miRNA), which reduces expression of a gene encoding sEH. Optionally, EETs may be administered in combination with such a nucleic acid. Typically, a study will determine the time following administration of the nucleic acid before a decrease is seen in levels of sEH. The EET or EETs are typically then administered at a time calculated to be after expression of the nucleic acid has resulted in a decrease in sEH levels.

Patients Who can Benefit from Use of EETs or sEHI or Both

The present methods find use in treating, i.e., reducing, relieving, ameliorating, preventing or inhibiting neuropathic pain in a subject or patient in need thereof. The patient may be subject to suffering neuropathic pain chronically or intermittently. The patient may or may not be exhibiting or experiencing symptoms of neuropathic pain at the nine of treatment. The neuropathic pain may be centrally or peripherally mediated.

Neuropathic pain results from a pathology in the nervous system. Notable features of neuropathic pain include (1) widespread pain not otherwise explainable; (2) evidence of sensory deficit; (3) burning pain; (4) pain to light stroking of the skin (allodynia); and (5) enhanced stimulus-dependent pain (hyperalgesia) and (6) attacks of pain without seeming provocation (stimulus-independent pain). Mechanisms of neuropathic pain are described, for example, in Zhuo, *Molecular Pain* (2007) 3:14; Campbell and Meyer, *Neuron* (2006) 52(1):77-92; Dworkin, et al., *Arch Neurol* (2003) 60:1524-34.

Neuropathic pain originates from a lesion of the nervous system. Any of a number of disease conditions or injuries can be the underlying cause of neuropathic pain. For example, the patient may be suffering from a metabolic disease (e.g., diabetic neuropathy), an autoimmune disease (e.g., multiple sclerosis), a viral infection (e.g. shingles and sequelae, postherpetic neuralgia), vascular disease (e.g. stroke), trauma and/or cancer. See, e.g. Campbell and Meyer, *Neuron* (2006) 52(1):77-92; Dworkin et al., *Arch Neurol* (2003) 60; 1524-34.

In some embodiments, the patient is suffering from peripheral neuropathic pain, for example, as a result of a disease condition including acute and chronic inflammatory demyelinating polyradiculoneuropathy; alcoholic polyneuropathy; chemotherapy-induced polyneuropathy; complex regional pain syndrome; entrapment neuropathies (e.g., carpal tunnel syndrome); HIV sensory neuropathy; iatrogenic neuralgias (e.g., postmastectomy pain or postthoracotomy pain); idiopathic sensor neuropathy; nerve compression or infiltration by tumor; nutritional deficiency-related neuropathies; painful diabetic neuropathy, phantom limb pain; postherpetic neuralgia; postradiation plexopathy; radiculopathy (cervical, thoracic, or lumbosacral); toxic exposure-related neuropathies; tic douloureux (trigeminal neuralgia); and/or posttraumatic neuralgias.

In some embodiments, the patient is suffering from central neuropathic pain, for example, as a result of a disease condition including compressive myelopathy from spinal stenosis; HIV myelopathy, multiple sclerosis-related pain; Parkinson disease-related pain; postischemic myelopathy; postradiation myelopathy; poststroke pain; posttraumatic spinal cord injury pain; and/or syringomyelia.

Neuropathic pain is distinguished from inflammatory pain in that it is not mediated by arachidonic acid, cyclooxygenases and prostaglandins. Therefore, neuropathic pain is not reduced or alleviated by non-steroidal anti-inflammatory agents, e.g., inhibitors of cyclooxygenases ("COX"), including selective COX-2 inhibitors.

In some embodiments of the invention, the person being treated with EETs, sEHI, or both, does not have hypertension or is not currently being treated with an anti-hypertension agent that is an inhibitor of sEH. In some embodiments, the person being treated does not have inflammation or, if he or she has inflammation, has not been treated with an sEH inhibitor as an anti-inflammatory agent. In some preferred embodiments, the person is being treated for inflammation but by an anti-inflammatory agent, such as a steroid, that is not an inhibitor of sEH. Whether or not any particular anti-inflammatory or anti-hypertensive agent is also a sEH inhibitor can be readily determined by standard assays, such as those taught in U.S. Pat. No. 5,955,496.

In some embodiments, the patient's disease or condition is not caused by an autoimmune disease or a disorder associated with a T-lymphocyte mediated immune function autoimmune response. In some embodiments, the patient does not have a pathological condition selected from type 1 or type 2 diabetes, insulin resistance syndrome, atherosclerosis, coronary artery disease, angina, ischemia, ischemic stroke. Raynaud's disease, or renal disease.

In some embodiments, the patient is not a person with diabetes mellitus whose blood pressure is 130/80 or less, a person with metabolic syndrome whose blood pressure is less than 130/85, a person with a triglyceride level over 215 mg/dL, or a person with a cholesterol level over 200 mg/dL, or is a person with one or more of these conditions who is not taking an inhibitor of sEH. In some embodiments, the patient does not have an obstructive pulmonary disease, an interstitial lung disease, or asthma.

In some embodiments, the patient is not also currently being treated with an inhibitor of one or more enzymes selected from the group consisting of cyclo-oxygenase (COX)-1, COX-2, and 5-lipoxygenase ("5-LOX"), or 5-lipoxygenase activating protein ("FLAP"). It is noted that many people take a daily low dose of aspirin (e.g., 81 mg) to reduce their chance of heart attack, or take an occasional aspirin to relieve a headache. Persons taking low dose aspirin to reduce the risk of heart attack are not currently known to take that aspirin in combination with an EET or sEHI to potentiate that effect. It is also contemplated that persons taking an occasional aspirin or ibuprofen tablet to relieve a headache or other episodic minor aches or pain would not ordinarily take that tablet in combination with an EET or sEHI to potentiate that pain relief. In some embodiments, therefore, the patient being treated by the methods of the invention may have taken an inhibitor of COX-1, COX-2, or 5-LOX in low doses, or taken such an inhibitor on an occasional basis to relieve an occasional minor ache or pain.

In some embodiments, the patient does not have dilated cardiomyopathy or arrhythmia.

In some embodiments, the patient is not applying EETs or sEHI topically for pain relief. In some embodiments, the patient is not administering. EETs or sEHI topically to the eye to relieve, for example, dry eye syndrome or intraocular pressure. In some embodiments, the patient does not have glaucoma or is being treated for glaucoma with agents that do not also inhibit sEH.

In some embodiments, the patient does not suffer from anxiety, panic attacks, agitation, status epilepticus, other forms of epilepsy, symptoms of alcohol or opiate withdrawal, insomnia, or mania. In some embodiments, the patient has one of the conditions listed in the last sentence, but is not being treated for the condition with an EET, an sEHI, or with both.

In some embodiments, the patient is not being treated for cancer of cells expressing peripheral benzodiazepine receptors (PBR) or $CB_2$ receptors. In some embodiments, a patient being treated for a cancer expressing such receptors is not being treated with an EET, an sEHI, or with both.

In some embodiments, the patient is not being treated to reduce oxygen radical damage. In some embodiments, a patient being treated to reduce oxygen radical damage is not being treated with an EET, an sEHI, or with both.

In some embodiments, the patient is not being treated for irritable bowel syndrome. In some embodiments, a patient being treated for irritable bowel syndrome is not being treated with an EET, an sEHI, or with both.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers can all be used in the methods of the invention, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides. The addition of water to the epoxides results in the corresponding 1,2-diols (Hammock, B. D. et al., in Comprehensive Toxicology: Biotransformation (Elsevier, N.Y.), pp. 283-305 (1997); Oesch, F. Xenobiotica 3:305-340 (1972)). Four principal EH's are known: leukotriene epoxide hydrolase, cholesterol epoxide hydrolase, microsomal EH ("mEH"), and soluble EH ("sEH," previously called cytosolic EH). The leukotriene EH acts on leukotriene A4, whereas the cholesterol EH hydrates compounds related to the 5,6-epoxide of cholesterol. The microsomal epoxide hydrolase metabolizes monosubstituted, 1,1-disubstituted, cis-1,2-disubstituted epoxides and epoxides on cyclic systems to their corresponding diols. Because of its broad substrate specificity, this enzyme is thought to play a significant role in ameliorating epoxide toxicity. Reactions of detoxification typically decrease the hydrophobicity of a compound, resulting in a more polar and thereby excretable substance.

"Soluble epoxide hydrolase" ("sEH") is an epoxide hydrolase which in many cell types converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). NCBI Entrez Nucleotide accession number L05779 sets forth the nucleic acid sequence encoding the protein, as well as the 5 untranslated region and the 3' untranslated region. The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Soluble EH is only very distantly related to mEH and hydrates a wide range of epoxides not on cyclic systems. In contrast to the role played in the degradation of potential toxic epoxides by mEH, sEH is believed to play a role in the formation or degradation of endogenous chemical mediators. Unless otherwise specified, as used herein, the terms "soluble epoxide hydrolase" and "sEH" refer to human sEH.

Unless otherwise specified, as used herein, the terms "sEH inhibitor" (also abbreviated as "sEHI") or "inhibitor of sEH" refer to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

By "physiological conditions" is meant an extracellular milieu having conditions (e.g. temperature, pH, and osmolarity) which allows for the sustenance or growth of a cell of interest.

"Micro-RNA" (miRNA") refers to small noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm C. elegans in the early 1990s and are now, known in many species, including humans. As used herein, it refers to exogenously administered mRNA unless specifically noted or otherwise required by context.

The term "co-administration" refers to the presence of both active agents in the blood at the same time. Active agents that are co-administered can be delivered concurrently (i.e., at the same time) or sequentially.

The terms "patient," "subject" or "individual" interchangeably refers to a mammal, for example, a human or a non-human mammal, including primates (e.g. macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The terms "reduce," "inhibit." "relieve" "alleviate." refer to the detectable decrease in symptoms of neuropathic pain, as determined by a trained clinical observer. A reduction in neuropathic pain can be measured by self-assessment (e.g., by reporting of the patient), by applying pain measurement assays well known in the art (e.g., tests for hyperalgesia and/or allodynia), and/or objectively (e.g., using functional magnetic resonance imaging or f-MRI). Determination of a reduction of neuropathic pain can be made by comparing patient status bet ore and after treatment.

Inhibitors of Soluble Epoxide Hydrolase

Scores of sEH inhibitors are known, of a variety of chemical structures. Derivatives in which the urea, carbamate, or amide pharmacophore (as used herein, "pharmacophore" refers to the section of the structure of a ligand that binds to the sEH) is covalently bound to both an adamantane and to a 12 carbon chain dodecane are particularly useful as sEH inhibitors. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci.

U.S.A, 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N-dodecyl urea ("ADU") is both metabolically stable and has particularly high activity on sEH, (Both the 1- and the 2-admamantyl ureas have been tested and have about the same high activity as an inhibitor of sEH.) Thus, isomers of adamantyl dodecyl urea are preferred inhibitors. It is further expected that N,N'-dodecyl-cyclohexyl urea (DCU), and other inhibitors of sEH, and particularly dodecanoic acid ester derivatives of urea, are suitable for use in the methods of the invention. Preferred inhibitors include:

12-(3-Adamantan-1-yl-ureido)dodecanoic acid (AUDA),

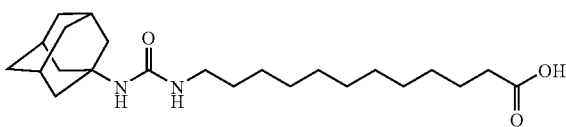 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE),

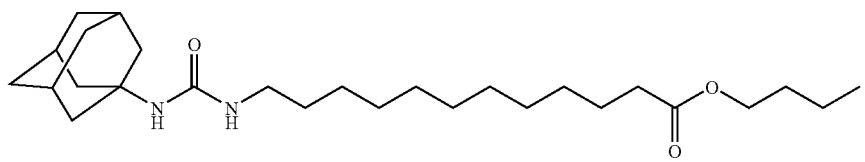 [SMILES: CCCCOC(=O)CCCCCCCCCCCNC(=O)NC12CC3CC(CC(C3)C1)C2]

Adamantan-1-yl-3-{5-[2-(2-ethoxyethoxy)ethoxy]pentyl}urea (compound 950, also referred to herein as "AEPU"), and

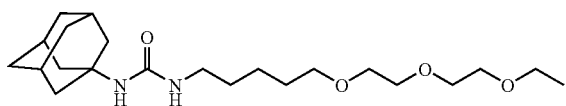 [SMILES: CCOCCOCCOCCCCCNC(=O)NC12CC3CC(CC(C3)C1)C2]

Another preferred group of inhibitors are piperidines. The following Table sets forth some exemplar piperidines and their ability to inhibit sEH activity, expressed as the amount needed to reduce the activity of the enzyme by 50% (expressed as "$IC_{50}$").

TABLE 1

$IC_{50}$ values for selected alkylpiperidine-based sEH inhibitors

| | | n = 0 | | n = 1 | |
|---|---|---|---|---|---|
| R: | | Compound | $IC_{50}$ (μM)$^a$ | Compound | $IC_{50}$ (μM)$^a$ |
| | H | I | 0.30 | II | 4.2 |
| | (isobutyl) | 3a | 3.8 | 4.a | 3.9 |
| | (pentyl) | 3b | 0.81 | 4b | 2.6 |

TABLE 1-continued

IC$_{50}$ values for selected alkylpiperidine-based sEH inhibitors

| R | n = 0 Compound | n = 0 IC$_{50}$ (μM)$^a$ | n = 1 Compound | n = 1 IC$_{50}$ (μM)$^a$ |
|---|---|---|---|---|
| n-butyl | 3c | 1.2 | 4c | 0.61 |
| benzyl | 3d | 0.01 | 4d | 0.11 |

$^a$As determined via a kinetic fluorescent assay.

A number of other sEH inhibitors which can be used in the methods and compositions of the invention are set forth in co-owned applications PCT/US2004/010298 and U.S. Published Patent Application Publication 2005/0026844.

U.S. Pat. No. 5,955,496 (the '496 patent) also sets forth a number of sEH inhibitors which can be used in the methods of the invention. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic add (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S,S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods of the invention are set forth in U.S. Pat. Nos. 6,150,415 (the '415 patent) and 6,531,506 (the '506 patent). Two preferred classes of sEH inhibitors of the invention are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty sEH inhibitors of Formula 2, which were shown to inhibit human sEH at concentrations as low as 0.1 μM. Any particular sEH inhibitor can readily be tested to determine whether it will work in the methods of the invention by standard assays. Esters and salts of the various compounds discussed above or in the cited patents, for example, can be readily tested by these assays for their use in the methods of the invention.

As noted above, chalcone oxides can serve as an alternate substrate for the enzyme. While chalcone oxides have half lives which depend in part on the particular structure, as a group the chalcone oxides tend to have relatively short half lives (a drug's half life is usually defined as the time for the concentration of the drug to drop to half its original value.

See, e.g. Thomas, G., Medicinal Chemistry: an introduction, John Wiley & Sons Ltd. (West Sussex, England, 2000)). Since the various uses of the invention contemplate inhibition of sEH over differing periods of time which can be measured in days, weeks, or months, chalcone oxides, and other inhibitors which have a half life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half lives although, for inhibitors with a relatively short half life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thin urea can be oxidized to dicyclohexylcarbodiimide which, with enzyme or aqueous acid (physiological saline), will form an active dicyclohexylurea. Alt natively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al. Journal of Agricultural and Food Chemistry, 21(5):747-751 (1973); Fahmy et al. Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Man methods of reducing the expression of genes, such as reduction of transcription and siRNA, are known, and are discussed in more detail below.

Preferably, the inhibitor inhibits sEH without also significantly inhibiting microsomal epoxide hydrolase ("mEH") Preferably, at concentrations of 500 µM, the inhibitor inhibits sEH activity by at least 50% while not inhibiting in mEH activity by more than 10%. Preferred compounds have an $IC_{50}$ (inhibition potency or, by definition, the concentration of inhibitor which reduces enzyme activity by 50%) of less than about 500 µM. Inhibitors with $IC_{50}$s of less than 500 µM are preferred, with $IC_{50}$s of less than 100 µM being more preferred and, in order of increasing preference, an IC50 of 50 µM, 40 µM, 30 µM, 25 µM, 20 µM, 15 µM, 10 µM, 5 µM, 3 µM, 2 µM, 1 µM or even less being still more preferred. Assays for determining sEH activity are known in the art and described elsewhere herein.

EETs

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has lone been believed that EETs administered systemically would be hydrolyzed too quickly by endogenous sEH to be helpful. For example, in one prior report of EETs administration. EETs were administered by catheters inserted into mouse aortas. The EETs were infused continuously during the course of the experiment because of concerns over the short half life of the EETs. See, Liao and Zeldin, International Publication WO 01/10438 thereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus. EETs can be administered without also administering an sEHI to provide a therapeutic effect. Moreover, we have found that EETs, if not exposed to acidic conditions or to sEH are stable and can withstand reasonable storage, handling and administration.

In short, sEHI, EETs, or co-administration of sEHIs and of EETs, can be used in the methods of the present invention. In some embodiments, one or more EETs are administered to the patient without also administering an sEHI. In some embodiments, one or more EETs are administered shortly before or concurrently with administration of an sEH inhibitor to slow hydrolysis of the EET or EETs. In some embodiments, one or more EETs are administered after administration of an sEH inhibitor, but before the level of the sEHI has diminished below a level effective to slow the hydrolysis of the EETs.

EETs useful in the methods of the present invention include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example. Sigma-Aldrich (catalog nos. E5516, E5641, and E5766, respectively, Sigma-Aldrich Corp. St. Louis, Mo.).

If desired, EETs, analogs, or derivatives that retain activity can be used in place of or in combination with unmodified EETs. Liao and Zeldin, supra, define FET analogs as compounds with structural substitutions or alterations in an EET, and include structural analogs in which one or more EET olefins are removed or replaced with acetylene or cyclopropane groups, analogs in which the epoxide moiety is replaced with oxirane or furan rings and heteroatom analogs. In other analogs, the epoxide moiety is replaced with ether, alkoxides, difluorocycloprane, or carbonyl, while in others, the carboxylic acid moiety is replaced with a commonly used mimic, such as a nitrogen heterocycle, a sulfonamide, or another polar functionality. In preferred forms, the analogs or derivatives are relatively stable as compared to an unmodified FET because they are more resistant than an unmodified EET to sEH and to chemical breakdown "Relatively stable" means the rate of hydrolysis by sEH is at least 25% less than the hydrolysis of the unmodified EET in a hydrolysis assay, and more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. En preferred forms, the analogs or derivatives have the biological activity of the unmodified EET regioisomer from which it is modified or derived in binding to the CB2 or peripheral BZD receptor. Whether or not a particular EET analog or derivative has the biological activity of the unmodified EET can be readily determined by using it in standard assays, such as radio-ligand competition assays to measure binding to the relevant receptor. As mentioned in the Definition section, above, for convenience of reference, the term "EETs" as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric, acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example. Robin Specialty Acrylics (Rohm America LLC, Piscataway, N.J.) under the trade name "Eudragit®". The choice of the particular enteric coating is not critical to the practice of the invention.

Assays for Epoxide Hydrolase Activity

Any of a number of standard assays for determining epoxide hydrolase activity can be used to determine inhibition of sEHI. For example, suitable assays are described in Gill, et al., Anal Biochem 131:273-282 (1983); and Borhan, et al., Analytical Biochemistry 231:188-200 (1995)). Suitable in vitro assays are described in Zeldin et al. J. Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids. Part B, (Law. III and H. C. Rifling, eds. 1985). Academic Press, Orlando, Fla., pp. 303-311 and Wixtrom et al. In: Biochemical Pharmacology and Toxicology, Vol. 1: Methodological Aspects of Drug Metabolizing Enzymes, (Zakim. D. and D. A. Vessey, eds. 1985), John Wiley & Sons, Inc., New York, pp. 1-93. Several spectral based assays exist based on the reactivity or tendency of the resulting diol product to hydrogen bond (see, Wixtrom, supra, and Hammock. Anal. Biochem. 174:291-299 (1985) and Dietze, et al. Anal. Biochem 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

Other Means of Inhibiting sEH Activity

Other means of inhibiting sEH activity or gene expression can also be used in the methods of the invention. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet, 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe, D. Curr Biol 9:R599-R601 (1999); Vaucheret et al. Plant J 16: 651-659 (1998)), RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)), in this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence, are set forth in Beetham et al., Arch. Biochem. Biophys. 305(1):197-201 (1993). The amino acid sequence of human sEH (SEQ ID NO:1) and the nucleotide sequence encoding that amino acid sequence (SEQ ID NO:2) are set forth in U.S. Pat. No. 5,445,956.

A program, siDESIGN from Dharmacon, Inc. (Lafayette. CO), permits predicting siRNAs for any nucleic acid sequence, and is available on the World Wide Web at dharmacon.com. Programs for designing siRNAs are also available from others, including Genscript (available on the Web at genscript.com/ssl-bin/app/mai) and, to academic and non-profit researchers, from the Whitehead Institute for Biomedical Research on the internet by entering "http://" followed by "jura.wi.mit.edu/pubint/http://iona.wi.mit.edu/siRNAext/."

For example, using the program available from the Whitehead institute, the following sEH target sequences and siRNA sequences can be generated:

```
1) Target:
CAGTGTTCATTGGCCATGACTCTGG      (SEQ ID NO: 3)

Sense-siRNA:
5'-GUGUUCAUUGGCCAUGACUTT-3'    (SEQ ID NO: 4)

Antisense-siRNA:
5'-AGUCAUGGCCAAUGAACACTT-3'    (SEQ ID NO: 5)

2) Target:
GAAAGGCTATGGAGAGTCATCTG        (SEQ ID NO: 6)

Sense-siRNA:
5'-AAGGCUAUGGAGAGUCAUCTT-3'    (SEQ ID NO: 7)

Antisense-siRNA:
5'-GAUGACUCUCCAUAGCCUUTT-3'    (SEQ ID NO: 8)

3) Target
AAAGGCTATGGAGAGTCATCTGC        (SEQ ID NO: 9)
```

```
Sense-siRNA:
5-AGGCUAUGGAGAGUCAUCUTT-3'     (SEQ ID NO: 10)

Antisense-siRNA:
5'-AGAUGACUCUCCAUAGCCUTT-3'    (SEQ ID NO: 11)

4) Target:
CAAGCAGTGTTCATTGGCCATGA        (SEQ ID NO: 12)

Sense-siRNA:
5-AGCAGUGUUCAUUGGCCAUTT-3'     (SEQ ID NO: 13)

Antisense-siRNA:
5'-AUGGCCAAUGAACACUGCUTT-3'    (SEQ ID NO: 14)

5) Target:
CAGCACATGGAGGACTGGATTCC        (SEQ ID NO: 15)

Sense-siRNA:
5'-GCACAUGGAGGACUGGAUUTT-3'    (SEQ ID NO: 16)

Antisense-siRNA:
5'-AAUCCAGUCCUCCAUGUGCTT-3'    (SEQ ID NO: 17)
```

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs front dsRNA using RNase III instead of dicer Like dicer, RNase 1.11 cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a. DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

1) Target:
(SEQ ID NO: 19)
CAGTGTTCATTGGCCATGACTGG

Sense strand;
(SEQ ID NO: 20)
5'-GATCCCCGTGTTCATTGGCCATGACTTTCAAGAGAAGTCATGGCCAA

TGAACACTTTTT-3'

Antisense strand:
(SEQ ID NO: 21)
5'-AGCTAAAAAGTGTTCATTGGCCATGACTTCTCTTGAAAGTCATGGCC

AATGAACACGGG-3'

2) Target:
(SEQ ID NO: 22)
GAAAGGCTATGGAGAGTCATCTG

Sense strand:
(SEQ ID NO: 23)
5'-GATCCCCAAGGCTATGGAGAGTCATCTTCAAGAGAGATGACTCTCCA

TAGCCTTTTTT-3'

Antisense strand:
(SEQ ID NO: 24)
5'-AGCTAAAAAAGGCTATGGAGAGTCATCTCTCTTGAAGATGACTCTC

CATAGCCTTGGG-3'

3) Target:
(SEQ ID NO: 25)
AAAGGCTATGGAGAGTCATCTGC

Sense strand:
(SEQ ID NO: 26)
5'-GATCCCCAGGCTATGGAGAGTCATCTTTCAAGAGAAGATGACTCTCC

ATAGCCTTTTT-3'

Antisense strand:
(SEQ ID NO: 27)
5'-AGCTAAAAAAGGCTATGGAGAGTCATCATCTCTTGAAAGATGACTCT

CCATAGCCTGGG-3'

4) Target:
(SEQ ID NO: 28)
CAAGCAGTGTTCATTGGCCATGA

Sense strand:
(SEQ ID NO: 29)
5'-GATCCCCAGCAGTGTTCATTGGCCATTTCAAGAGAATGGCCAATGAA

CACTGCTTTTT-3'

Antisense strand:
(SEQ ID NO: 30)
5'-AGCTAAAAAAGCAGTGTTCATTGGCCATTCTCTTGAAATGGCCAATG

AACACTGCTGGG-3'

5) Target:
(SEQ ID NO: 31)
CAGCACATGGAGGACTGGATTCC

Sense strand
(SEQ ID NO: 32)
5'-GATCCCCGCACATGGAGGACTGGATTTTCAAGAGAAATCCAGTCCTC

CATGTGCTTTTT-3'

Antisense strand:
(SEQ ID NO: 33)
5'-AGCTAAAAAGCACATGGAGGACTGGATTTCTCTTGAAAATCCAGTCC

TCCATGTGCGGG-3'

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid, sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the tame gene (see, e.g., Cheng et al., 1988, J. Biol. Chem. 263:15110; Ferrin and Camerini-Otero, 1991, Science 354:1494; Ramdas et al., 1989, J. Biol. Chem. 264.17395; Strobel et al., 1991. Science 254:1639; and Rigas et al., 1986. Proc. Natl. Acad. Sci. U.S.A. 83:9591)

Antisense molecules can be designed by methods known in the art. For example, Integrated DNA Technologies (Coralville, Iowa) makes available a program on the internet which can be found by entering http://, followed by biotools.idtdna.com/antisense/AntiSense.aspx, which will provide appropriate antisense sequences for nucleic acid sequences up to 10.000 nucleotides in length. Using this program with the sEH gene provides the following exemplar sequences:

| 1) UGUCCAGUGCCCACAGUCCU | (SEQ ID NO: 34) |
| 2) UUCCCACCUGACACGACUCU | (SEQ ID NO: 35) |
| 3) GUUCAGCCUCAGCCACUCCU | (SEQ ID NO: 36) |
| 4) AGUCCUCCCGCUUCACAGA | (SEQ ID NO: 37) |
| 5) GCCCACUUCCAGUUCCUUUCC | (SEQ ID NO: 38) |

In another embodiment, ribozymes can be designed to cleave the mRNA at a desired position. (See. e.g., Cech, 1995, Biotechnology 13:323; and Edgington, 1992, Biotechnology 10:256 and Ku et al., PCT Publication WO 94/03596%).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the non coding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991. Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocation carriers. For example, homeodomain proteins have the ability to translocate across cell membranes. The shortest internalizable peptide of a homeodomain protein. Antennapedia, was found to be the third helix of the protein, from amino acid position 43 to 58 (see, e.g., Prochiantz. Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found by entering "www." followed by "nature.com/news/2005/0504184/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among, related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11):4006-9 (2005); Brennecke et al., PLoS Biol. 3(3):e85 (2005). Methods of designing miRNAs are known. See, e.g., Zeng al., Methods Enzymol. 392:371-80 (2005); Krol et al., J. Biol. Chem. 279(40):42230-9 (2004); Ying and Lin, Biochem Biophys Res Commun. 326 (3):515-20 (2005).

Therapeutic Administration

EETs and inhibitors of sEH can be prepared and administered in a wide variety of oral, parenteral and aerosol formulations. In some preferred forms, compounds for use in the methods of the present invention can be administered by injection, that is, intravenously, intramuscularly, intracutaneously, subcutaneously, intradermally, intrathecally, intraduodenally, or intraperitoneally while in others, they are administered orally. Administration can be systemic or local, as desired. The sEH inhibitor or EETs, or both, can also be administered by inhalation. Additionally, the sEH inhibitors, or EETs, or both, can be administered transdermally. Accordingly, the methods of the invention permit administration of pharmaceutical compositions comprising a pharmaceutically acceptable carrier or excipient and either a selected inhibitor or a pharmaceutically acceptable salt of the inhibitor.

For preparing pharmaceutical compositions from sEH inhibitors, or EETs, or both, pharmaceutically acceptable carriers can be either solid or liquid. Solid form preparations include powders, tablets, pills, capsules, cachets, suppositories, and dispersible granules. A solid carrier can be one or more substances which ma also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier had the necessary binding, properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of the sEH inhibitor, or EETs, or both, is employed in reducing, alleviating, relieving, ameliorating, preventing and/or inhibiting neuropathic pain. The dosage of the specific compound for treatment depends on many factors that are well known to those skilled in the art. They include for example, the route of administration and the potency of the particular compound.

Determination of an effective amount is well within the capability of those skilled in the art Generally, an efficacious or effective amount of a sEH inhibitor or an EET is determined by first administering a low dose or a small amount of either a sEH inhibitor or an EET, and then incrementally increasing the administered dose or dosages, adding a second medication as needed, until a desired effect of is observed in the treated subject with minimal or no toxic side effects. An exemplary dose is from about 0.001 µM/kg to about 100 mg/kg body weight of the mammal. sEH inhibitors with lower IC50 concentrations can be administered in lower doses.

EETs are unstable in acidic conditions, and can be converted to DHETs. To avoid conversion of orally administered EETs to DHETs under the acidic conditions present in the stomach, EETs can be administered intravenously, by injection, or by aerosol. EETs intended for oral administration can be encapsulated in a coating that protects the EETs during passage through the stomach. For example, the EETs can be provided with a so-called "enteric" coating, such as those used for some brands of aspirin, or embedded in a formulation. Such enteric coatings and formulations are well known in the art. In some formulations, the EETs, or a combination of the EETs and an sEH inhibitor are embedded in a slow-release formulation to facilitate administration of the agents over time.

In another set of embodiments, an sEH inhibitor, one or more EETs, or both an sEH inhibitor and an EET are administered by delivery to the nose or to the lung. Intranasal and pulmonary delivery are considered to be ways drugs can be rapidly introduced into an organism. Devices for delivering drugs intranasally or to the lungs are well known in the art. The devices typically deliver either an aerosol of an therapeutically active agent in a solution, or a dry powder of the agent. To aid in providing reproducible dosages of the agent, dry powder formulations often include substantial amounts of excipients, such as polysaccharides, as bulking agents.

Detailed information about the delivery of therapeutically active agents in the form of aerosols or as powders is available in the art. For example, the Center for Drug Evaluation and Research ("CDER") of the U.S. Food and Drug Administration provides detailed guidance in a publication entitled: "Guidance for Industry: Nasal Spray and Inhalation Solution, Suspension, and Spray Drug Products—Chemistry, Manufacturing, and Controls Documentation" (Office of Training and Communications. Division of Drug Information, CDER, FDA, July 2002). This guidance is available in written form from CDER, or can be found on-line by entering "http://www." followed by "fda.gov/cder/guidance/4234fnl.htm". The FDA has also made detailed draft guidance available on dry powder inhalers and metered dose inhalers. See, Metered Dose inhaler (MDI) and Dry Powder Inhaler (DPI) Drug Products—Chemistry, Manufacturing, and Controls Documentation, 63 Fed. Reg. 64270, (November 1998). A number of inhalers are commercially available, for example, to administer albuterol to asthma patients, and can be used instead in the methods of the present invention to administer the sEH inhibitor, EET, or a combination of the two agents to subjects in need thereof.

In some aspects of the invention, the sEH inhibitor, EET, or combination thereof, is dissolved or suspended in a suitable solvent, such as water, ethanol, or saline, and administered by nebulization. A nebulizer produces an aerosol of fine particles by breaking a fluid into fine droplets and dispersing them into a flowing, stream of gas. Medical nebulizers are designed to convert water or aqueous solutions or colloidal suspensions to aerosols of fine, inhalable droplets that can enter the lungs of a patient during inhalation and deposit on the surface of the respiratory airways. Typical pneumatic (compressed gas) medical nebulizers develop approximately 15 to 30 microliters of aerosol per liter of gas in finely divided droplets with volume or mass median diameters in the respirable range of 2 to 4 micrometers. Predominantly, water or saline solutions are used with low solute concentrations, typically ranging from 1.0 to 5.0 mg/int.

Nebulizers for delivering an aerosolized solution to the lungs are commercially available from a number of sources, including the AERx™ (Aradigm Corp., Hayward, Calif.) and the Acorn II® (Vital Signs Inc., Totowa, N.J.).

Metered dose inhalers are also known and available. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; and 4,896,832.

The formulations may also be delivered using a dry powder inhaler (DPI), i.e., an inhaler device that utilizes the patient's inhaled breath as a vehicle to transport the dry powder drug to the lungs. Such devices are described in, for example, U.S. Pat. Nos. 5,458,135; 5,740,794; and 5,785,049. When administered using a device of this type, the powder is contained in a receptacle having a puncturable lid or other access surface, preferably a blister package or cartridge, where the receptacle may contain a single dosage unit or multiple dosage units.

Other dry powder dispersion devices for pulmonary administration of dry powders include those described in Newell, European Patent No. EP 129985; in Hodson, European Patent No. EP 472598, in Cocozza, European Patent No. EP 467172, and in Lloyd, U.S. Pat. Nos. 5,522,385; 4,668,281; 4,667,668; and 4,805,811. Dry powders ma also be delivered using, a pressurized, metered dose inhaler (MDI) containing a solution or suspension of drug in a pharmaceutically inert liquid propellant, e.g., a chlorofluorocarbon or fluorocarbon, as described in U.S. Pat. Nos. 5,320,094 and 5,672,581.

Without further elaboration, it is believed that one skilled in the art can, using the preceding description, practice the present invention to its fullest extent.

EXAMPLES

Example 1

FIG. 1 shows that neuropathy was indeed induced, in the tested animals per group). When animals were treated with streptozocin, they showed a drastic reduction in their withdrawal latencies in a chronic manner (FIG. 1). This effect was very stable over the course of several months. Subsequent application of the sEHI AUDA reduced neuropathic pain in a dose and time dependant manner. This was evident in two independent pain tests. FIG. 2 shows the dose and time response relationship of AUDA and compound 1010 in neuropathic rats as determined using the von Frey test. Administration of AUDA at a moderate dose completely reversed the decrease in withdrawal threshold. The decrease in withdrawal threshold is an established and reliable indicator of analgesic activity. The activity of AUDA followed the plasma concentrations of the drug. AUDA lost its effect after four hours.

The results of the mechanical hyperalgesia test were in parallel to the observation with the mechanical allodynia test. As shown in FIG. 3, AUDA reduced pain in a time and dose dependant (10, 20 and 50 mg/kg) manner, whereas a compound inactive in inhibiting sEH (e.g. compound 1010) showed no effectiveness at 25 mg/kg.

We conclude from these results that inhibition of sEH is analgesic for neuropathic pain. Without wishing to be bound by theory, it is believed that this analgesic effect is due not only to the anti-inflammatory activity of sEHIs hut also because an increase in EETs and other epoxygenated endogenous compounds cause a direct action on nociceptors, thereby reducing pain in general. Given that inflammation is not involved in streptozocin induced diabetic neuropathy, in this model the anti-inflammatory effects of sEHIs are negligible.

Example 2

This Example sets forth the materials and methods used in the studies reported in Example 1.

Male Sprague-Dawley rats weighing 250-300 grains were used. Animals were individually housed at UC Davis Animal Resource Facility under standard conditions with free access to food and water, and maintained for at least 1 week before the experiments. Pain was quantified using three tests, the hind paw withdrawal latency test, the mechanical hyperalgesia test and the mechanical allodynia test. All the experiments were performed during the daytime.

Rats were first trained to the experimental chamber in two separate sessions. On the day of the induction of neuropathy, the animals' basal response to all three tests were measured and then streptozocin (50 mg/kg) was administered intravenously. Animals were then followed over time for the development of neuropathic pain. An inhibitor of sEH was administered subcutaneously one week after the onset of pain symptoms. A dose response study was conducted where increasing dose of the sEHI AUDA was tested along with an inactive control compound (e.g. compound 1010). Pain response was measured at 60, 120, 240 and 480 minutes after the administration of the sEHI. Compounds were formulated by dissolving them in ethanol and mixing with trans free oleic oil. At least six animals per group were used. The Von Frey test was conducted by stimulating the plantar surface of the rats' hind paw with a calibrated filament connected to a force transducer. As this filament is applied the amount of force exerted on the paw increases and the animal withdraws its paw when the force reaches its threshold. The force this moment is displayed electronically with a display connected to the force transducer. In the Randal-Selitto test a similar principle is used. The animals' hind paw is placed between a flat surface and a pointed tip of a force transducer. The pointed tip exerts force on the dorsal face of the paw. The amount of force applied is increased linearly until the animal withdraws and the force displayed is counted as the threshold. The two tests are complementary, but depend on the activity of different groups of nociceptors.

Similar results were obtained using structurally different chemical inhibitors of sEH. Two novel sEHIs, TPAU and t-AUCB, both reduced and at higher doses eliminated) streptozocin induced neuropathic pain in a time and dose dependent manner (FIGS. 4 and 5).

Example 3

While monitoring epoxy/diol ratios of plasma fatty acids as a blood marker of efficacy, we surprisingly found an extensive reduction in pro-inflammatory fatty acid metabolites in severely inflamed mice treated with sEHI. These remarkable decreases particularly in $PGE_2$ production compelled us to test if EETs and/or sEHI could reduce inflammatory pain. We found that both compounds alone and in combination were highly potent analgesic agents in rodents systemically or topically. AEPU, an early prototype sEH inhibitor, at 50 mg/kg, administered dermally, transiently increased the paw withdrawal latency of animals treated with intraplantar LPS in response to a mild heat stimulus. AEPU is metabolized rapidly but the temporal analgesic activity correlates with blood inhibitor levels. Another sEHI, TPAU, at 10 mg/kg showed a potency strikingly comparable to that of a moderate dose of morphine (1 mg/kg) but was clearly superior because of its better pharmacodynamics. TPAU treated animals showed no reduction in response to stimuli or gross signs of loss of motor activity.

sEH Inhibitors Transcriptionally Down Regulate Spinal COX-2 Expression

During sepsis or local inflammation increased plasma $PGE_2$ levels were still prevalent upon sEHI treatment, although diminished considerably. Thus it was not clear if observed analgesia was solely based on this decrease. In fact, when we co-administered sub-therapeutic doses of selective cox-2 inhibitors with sEHIs despite an apparent synergistic reduction in plasma $PGE_2$ a comparable synergistic improvement in analgesic scores was not evident; the analgesic effect, was additive. Nevertheless, under inflammatory conditions diverting the flow of AA from COX branch towards the P450 branch resulted with health benefits including enhanced anti-inflammatory activity and decreased risk of thrombotic events because of the normalization of prostacylin to thromboxane ratio by sEHIs. Noxious stimuli have long been established to evoke overproduction of prostanoids in the spinal cord. Likewise, we determined the temporal expression of cox-2 in the spinal cord of rats in response to peripheral inflammation and asked if cox-2 message is influenced by sEH inhibitors in the CNS. We observed a highly significant increase in COX-2 mRNA in the spinal cord with intraplantar LPS administration. Two structurally distinct, potent sEHIs extensively attenuated this increase in the rat CNS as was observed in mouse liver earlier. We then asked if the gene expression changes correlated to behavioral pain scores. Neither the two inhibitors nor LPS treatment displayed a temporal correlation between spinal COX-2 expression and pain scores. AEPU, had a transient effect on pain however remained analgesic as COX-2 message was increasing over time, whereas systemic t-PAU, even as a less potent inhibitor in vitro, was particularly more effective both in decreasing pain related behavior and down regulating COX-2 expression.

It was not surprising in the case of LPS treated animals to observe a poor correlation between COX-2 expression and pain scores because inflammation evokes a cascade of reactions including the release of numerous pronociceptive mediators with overlapping yet distinct temporal and spatial occurrence. Whereas administration of selective COX inhibitors peripherally or centrally correlate well with analgesia, sEH inhibitors displayed a profile indicative of an alternate mechanism in addition to transcriptionally down regulating COX-2. Of note, t-PAU substantially reduced hyperalgesia prior to extensive induction of spinal COX-2. As a control, we tested sEHIs on a neuropathic pain model. We expected no activity, but observed dose and time dependent improvement in pain scores of diabetic rats with another prototype sEHI, AUDA(rat sEH IC50 2.1 nM) not with a far less potent sEHI hydroxyl-AEPU (an inactive metabolite, of AEPU, rat sEH IC50 1164 nM), although the two compounds share structural similarities and pharmacodynamic properties.

EETs Bind to TSPO

These results led us to look at a larger number of potential targets and we screened the binding of EETs against a set of cellular receptors. Given that EETs are highly hydrophobic and significantly similar in structure to ubiquitous fatty acids it was surprising to observe affinity towards only three receptors out of 48 targets. Of these potential targets we focused on the translocator protein TSPO formerly known as the peripheral or mitochondrial benzodiazepine receptor. The mixture of synthetic EETs or their methyl ester analogs (EET-me) displaced a high affinity radioligand, $[^3H]$ PK 11195, from the TSPO with an IC50 of 4.6 µM without affecting $[^3H]$-flunitrazepam binding to central benzodiazepine receptors up to a concentration of 100 µM 19. Two of the individual regioisomers, the 5,6-EET-me and the 14,15-EET-me, although less potent than the mixture were active and more efficacious on this receptor whereas one regioisomer, the 8,9-EET-me, completely lacked activity. The major proposed biological function of the TSPO is its involvement in steroidogenesis as this protein is essential for the rate limiting step of translocation of cholesterol from the outer to the inner mitochondrial membrane for downstream synthesis of steroids in the peripheral tissues and primarily neurosteroids in the nervous tissue. Several lines of evidence suggest that cholesterol import into the mitochondria is executed by a protein complex that may involve the formation of the mitochondrial membrane permeability transition pore (MPTP) and is composed of as complex of proteins including TSPO, VDAC (voltage dependant anion channel), PAP7 (PBR associated protein) and StAR (steroidogenic acute regulatory protein). Interestingly TSPO ligands were found to have anti-inflammatory effects.

Steroid Synthesis but not Steroid Receptors is Required for sEHI Mediated Analgesia The displacement of the $[^3H]$ PK 11195 from its binding site by EETs, while demonstrated a potential interaction with EETs and TSPO or a component of MPTP, did not reveal if EETs are agonistic or antagonistic in regard to the biological activity of this receptor. In addition the observed effective concentration values were far higher than what would be considered a tight receptor-ligand interaction. Interestingly, EETs have been shown to stimulate cortisol production in isolated bovine adrenal fasciculata cells or estradiol production in cultures of human luteinized granulose cells. Accordingly, we surmised EETs activate TSPO and tested the hypothesis that some of the analgesic effects of synthetic sEHIs and natural EETs on pain are through an increase in the production of analgesic neurosteroids in the CNS. We predicted that inhibition of acute steroidogenesis would antagonize the analgesic effect of sEHIs and tested this in vivo using two steroid synthesis inhibitors that target steroidogenesis at different levels subsequent to cholesterol import into the mitochondria. The analgesic activity of AEPU was completely abolished when aminoglutethimide (10 mg/kg, dermal), a general steroidogenesis inhibitor or finasteride (10 mg/kg, dermal), a CNS permeable 5α reductase inhibitor were co-administered with AEPU. These antagonists however had no significant effect on the development of UPS induced hyperalgesia nor did they have any affect on vehicle treated animals' thermal withdrawal thresholds possibly because the circulating hormones were not completely depleted by these inhibitors during the short time frame of the experiment.

Next, we took a two pronged approach. We tested the requirement of steroid receptors on sEHI mediated analgesia and also quantified two major circulating steroids from plasma. The possibility that circulating steroids are required for the analgesic action of AEPU is unlikely because none of the tested glucocorticoid/progesterone, mineralocorticoid, androgen and estrogen receptor antagonists (10 mg/kg, dermal) significantly reversed the sEHI mediated analgesia. Independently, local UPS rather than sEHI caused a surge in circulating progesterone and no change occurred in testosterone levels among treatments. These results decrease the possibility of a general increase in steroidogenesis or an activity of AEPU through steroid mediated gene expression.

EETs and sEH Inhibitors Enhance Spinal StAR Expression

The stimulating effect of AA, its lipoxygenases and cytochrome P450 generated metabolites on steroidogenesis have been recognized as early as the 1980s. Previously at least part of this effect was traced to EETs which stimulate cortisol production and recently EETs were shown to directly increase StAR gene expression and steroid synthesis in cell lines from the reproductive tissues. It is proposed that TSPO and phosphorylated de novo StAR cooperatively facilitate the acute transport of cholesterol into the mitochondria. We asked whether inhibition of sEH also enhanced the expression of StAR mRNA. In the two major peripheral steroidogenic tissues, we observed StAR mRNA levels 5000 and 37000 fold higher in testis and adrenal glands than that of spinal cord or brain. Whereas adrenal and testis StAR mRNA changes corresponded well to circulating progesterone and testosterone levels, no enhancement by sEH above that of inflammation was present.

In the CNS, we found the spinal cord StAR expression was briefly increased during inflammation parallel to the increase in adrenal StAR, suggesting the potential existence of an endogenous analgesic coping mechanism. This is in corroboration with the recent finding that synaptic inhibition through GABAA receptor activity in lamina II of the dorsal horn was enhanced during inflammatory pain because of an increase in endogenously produced 5α-reduced neurosteroids in a fashion that can be reversed with finasteride application. However we focused our efforts on the influence of inhibiting sEH upon StAR expression; two structurally dissimilar sEHIs strikingly enhanced the increase in StAR message up to 8 fold. In contrast to the lack of correlation between a decrease in COX-2 message and analgesia index, the increase in StAR message strongly and positively correlated with the temporal occurrence of analgesia upon sEHI intervention with AEPU ($r^2=0.94$) and moderately with t-PAU ($r^2=0.49$). For t-PAU, the lower magnitude of correlation could stem from a ceiling effect or superior downregulation of COX-2. In saggital brain slices encompassing the proximal two thirds of the brain StAR message per GAPDH message levels were identical to those quantified from the spinal cord. However, neither local inflammation nor AEPU alone elicited an increase in StAR message in the brain, although a two fold increase in inflamed animals treated with AEPU was evident. These findings implicate a specific pattern of regulation of steroidogenesis by sEH inhibitors and/or EETs.

sEHIs and EETs Divert Elevated cAMP to an Analgesic Pathway

The maintenance of hyperalgesia in inflammatory and neuropathic pain states is known to be largely regulated by the activation of the cAMP signaling pathways. In the brain, levels of intracellular cAMP are known to rise rapidly in response to inflammation mainly because of the COX-2 product PGE2, which upon binding activates its EP receptors and initiates a cascade of events starting with stimulation of adenylate cylase to kinase activation and gene expression. The resulting, inflammatory pain can conveniently be blocked by an inactive cAMP analogue which prevents PKA activation. Although the prevailing outcome of elevated intracellular cAMP in the nociceptive cells seems to be a sustained pain state we hypothesized that increasing the levels of endogenous EETs may favor neurosteroid production to override nociceptive signaling. Specifically, an important requirement for the interaction between EETs. TSPO activity and StAR expression may be the presence of elevated cAMP because expression and phosphorylation of StAR is greatly enhanced upon tropic hormone stimulation which increases cAMP levels although the basal expression of StAR is independent of cAMP.

We assessed the increase in spinal intracellular cAMP upon inflammation by quantifying the expression of ICER, an immediate early transcription factor known to be up regulated rapidly upon a rise in intracellular cAMP level. Whereas LPS treatment led to a brief but meaningful increase, AEPU treatment enhanced and maintained the increase in ICER message up to 3 fold in the spinal cord. Inferring that the concurrent presence of cAMP and EETs may be required for neurosteroid based analgesia, we tested this hypothesis by quantifying StAR expression in response to cAMP, EETs and a potent sEH inhibitor. A high quantity of membrane permeable 8-Br cAMP (100 µg) was administered into the spinal cord and rapid (30 min.) expression of SCAR mRNA in the spinal cord and the brain was quantified in the presence of basal and increased EET levels. As expected, intrathecal co-administration of 8-Br cAMP and EETs (5 µg) significantly increased StAR levels in the spinal cord, AEPU (1 µg), as well increased the expression level of StAR in the spinal cord when administered together with 8-Br cAMP. Because AEPU is many fold more stable than EETs in vivo, this sEHI elicited a parallel increase in the brain whereas intrathecal EETs had no affect on brain StAR mRNA. StAR expression in both tissues did not change within 30 minutes in response to saline, 8-Br cAMP or AEPU alone. These observations may explain the lower potency of sEHIs in the absence of inflammation or neuropathy when intracellular cAMP levels are inadequate to drive neurosteroid production.

Although our purpose was not to delineate a novel neurosteroid based endogenous analgesic pathway, several lines of evidence suggest the occurrence of such a pathway. Acute inflammation in our model caused a substantial and parallel increase in StAR expression both in the spinal cord and the adrenal gland. Given that adrenal StAR increase is accompanied by a surge in circulating progesterone levels, we are compelled to propose that a parallel increase in progesterone, the intermediate for neurosteroid production, may occur in the spinal cord. The tightly regulated nature of a potential TSPO/StAR based analgesic pathway is evident from the observations that the presence of elevated EETs and cAMP are both required to achieve StAR upregulation Taken together, the hallmark of sEHI mediated analgesia could be that sEHIs afford the sustenance of a higher level of TSPO activation and/or StAR expression upon stabilizing EETs and enhance the production of unidentified factors, presumably neurosteroids, in the CNS which modulate nociceptive signaling. Because an increase in intracellular cAMP levels in many pain states, both inflammatory and neuropathic, is correlated with the occurrence of pain, we predict inhibition of sEH may broadly result in analgesia in a diverse number of pain models.

The analgesic, anesthetic and antidepressant activities of neurosteroids are well described. However until now there was no clear course towards regulating the levels of these molecules. Here, we show that activating TSPO and/or diverting the flow of increased intracellular cAMP towards upregulation of StAR message in the CNS by way of inhibiting sEH is a feasible path to accomplish analgesia in inflammatory and neuropathic pain states.

Example 4

This Example sets forth materials and methods used in the studies discussed in Example 3.

Animals and chemicals. This study was approved by the UC Davis Animal Care and Use Committee. Male Sprague-Dawley rats weighing 250-350 g were obtained from Charles River Inc., and maintained in UC Davis animal housing facilities with ad libitum water and food under standard conditions. The sEH inhibitor AEPU was synthesized in our laboratory as described previously (Morisseau et al. 2002 and Kim et al. 2004), EET-methyl esters and free acids were synthesized using arachidonic acid methyl ester or free acid and purified as described previously (Campbell et al, 1991). The mixture was characterized by LC-MS/MS as described (Smith et al. 2005). All chemicals were from Sigma-Aldrich (St. Louis, Mo.). Compounds were formulated into Vanicream™ (Pharmaceutical Specialties, Inc. Rochester, Minn.) for topical administration, into trans free oleic oil or saline for subcutaneous and intrathecal administration.

Binding studies. Radioligand binding studies were conducted by CEREP (France) according to standard procedures as described by LeFur. Briefly, rat heart mitochondria was isolated and incubated with [$^3$H] PK11195 at 30° C. in the presence of increasing concentrations of EET-me analogues or EET free acids. Reaction mixture was passed through glass wool filters washed 3 times using cold binding buffer and dried by air. Filter were than counted and $IC_{50}$ values were calculated.

Treatments and behavioral nociceptive tests. Behavioral nociceptive testing was conducted by assessing thermal hindpaw withdrawal latencies (TWL) using a commercial Hargreaves (Hargreaves et. al 1998) apparatus (IITC, Woodland Hills, Calif.), or by determining mechanical hindpaw withdrawal thresholds (MWT) using an electronic von Frey anesthesiometer (IITC, Woodland. Hills, Calif.). For DAT determination, a maximum stimulus duration of 22 s was imposed to prevent tissue damage. Following baseline measurements, rats were first treated with 200 μl of vehicle or compound-formulated cream by topical application to one hindpaw, LPS (10 g in 50 μl 0.9% NaCl) was injected into the plantar surface of the treated paw. For subcutaneous administration, compounds were injected immediately after intraplantar LPS. Animals were then placed in acrylic chambers on a glass platform maintained at a temperature of 30±1° C. for measurement or on a wire-mesh platform for MWT measurements. A probe fitted with a filament that is connected to a force transducer was applied to the plantar hind paw surface through a wire-mesh platform until eliciting a withdrawal reflex. The duration of heat application or the force (gr) necessary to elicit a withdrawal was designated as TWL and MWT. The steroidogenesis inhibitors were applied 2 hours before sEHI and LPS administration. Diabetes was induced by intravenous injection of 50 mg/kg streptozocin (STZ) in saline following baseline measurements. Diabetic animals were tested at least one week after STZ administration. Three measurements were taken from each animal at each time point and average responses were converted to percent analgesia index based on each animals' baseline response.

Sample Collection, Extraction, Analysis

Blood samples for chemical analysis were collected by cardiac puncture under deep isoflurane anesthesia. Plasma was immediately separated by centrifuging at 4000 rpm for 10 minutes in a cold centrifuge. Rats were then decapitated under anesthesia and tissues were removed and flash frozen in liquid nitrogen. For sampling the brain after decapitation, the scalp was first removed providing accessibility to the cranial plates. A midline incision was introduced to detach the cranial plates and brain was carefully exposed by peeling the plates. The brain was removed from the skull using a spatula, immediately placed in liquid nitrogen, and stored at −80° C. The prefrontal area was removed by a coronal cut to the distal one third of the brain from the frozen tissue. The cerebellum was also removed and the brain was hemisected. Saggital slices with a thickness of 2 mm and weighing 100-200 mg were cut from both hemispheres lateral to the thalamus and stored to be used for qRT-PCR or chemical analysis. Plasma hormone levels were quantified using RIA. For quantitative RT-PCR, standard procedures were followed.

Lipid extractions and oxylipin concentrations were measured according to Schmelzer et al. (2005). Briefly, oxylipins were extracted from plasma via Oasis SPE, dried under nitrogen and reconstituted in 50 μl MeOH:water (75:25) containing internal standards. Oxylipids extracts were separated by reverse-phase HPLC on an XTerra MS C18 column [30×2.1 mm i.d., 3.5 μm (Waters, Milford, Mass.)] and quantified with a Quattro Ultima tandem quadrupole mass spectrometer (Micromass, Manchester, UK) in negative mode electrospray ionization and multiple reaction monitoring.

To quantify compound plasma levels, serial tail bleed samples of 20-50 μl blood were collected into heparin-treated tubes. For urine quantification, 500 μL of urine was collected at various time points (2 to 24 hr) and immediately frozen. The samples were then transferred to a 1.5 mL microcentrifuge tube, weighed and mixed with 100 μL of purified water and 25 μL of surrogate (100 ng/mL CUDA N-cyclohexyl-N_-dodecanoic acid urea) and vortexed. The samples were extracted with 500 μL of ethyl acetate. The organic layer was then transferred to a 1.5 mL microcentrifuge tube, and dried under nitrogen. The residues were reconstituted in 25 μL of methanol and 10 μL aliquots were injected to the LC/MS/MS system. An XTerra™ MS $C_{18}$ column (30×2.1 mm I. D., 3.5 μm; Waters Corporation) was used with a flow rate of 0.3 mL/min at ambient temperature. The ESI mass spectrometer was operated in the positive ion mode with a capillary voltage at 1.0 kV. Cone gas ($N_2$) and desolvation gas ($N_2$) were maintained at flow rates of 130 and 630 L/h, respectively. The source and the desolvation temperature were set at 100 and 300° C., respectively. Optimum cone voltages were set at 80 V for 12-(3-adamantan-1-yl-ureido)-butyric acid (also referred to herein as "AUBA"), AUDA, IK 950 and 950-OH and 85 V for CUDA.

Statistical Analyses

For TWL and MWT measurements, within group comparisons were performed using a two-factor ANOVA (animal× timepoint) followed by two-sided Dunnett multicomparisons using commercial statistical software (SPSS, Chicago, Ill.). Between-group comparisons of TWLs and MWTs were performed using a two-tailed Student's t-test. Because von Frey gradations consist of non-linear increases in bending force, a log-transform was performed on the MWT data before running statistical analyses.

REFERENCES

1. Vane J R, Inhibition of prostaglandin synthesis as a mechanism of action for aspirin-like drugs. Nat New Biol 231 232-235. (1971).
2. McGiff J C, Cytochrome P-450 Metabolism of Arachidonic Acid. Annual Review of Pharmacology and Toxicology 31:339-369 (1991).
3. Spector A A and Norris A W, Action of epoxyeicosatrienoic acids (EETs) on cellular function. American Journal of Physiology—Cell Physiology:00402.02006 (2006).

4. Vane J R, Bakhle Y S and Botting R M, Cyclooxygenases 1 and 2, pp 97-120 (1998
5. Capdevila J, Falck J R, Estabrook R W., Cytochrome P450 and the arachidonate cascade. FASEB JOURNAL 6:731-736 (1992).
6. Meyer R A, Davis K D, Cohen R H, Treede R-D and Campbell J N, Mechanically insensitive afferents (MIAs) in cutaneous nerves of monkey. Brain Research 561; 252-261 (1991).
7. Campbell W, Brady, M T. Rosolowsky, L J, Falck, J R., Metabolism of arachidonic acid by rat adrenal glomerulosa cells: synthesis of hydroxyeicosatetraenoic acids and epoxyeicosatrienoic acids. Endocrinology 128:2183-2194 (1991).
8. Snider N T, Kornilov A M, Kent U M and Hollenberg P F, Anandamide Metabolism by Human Liver and Kidney Microsomal Cytochrome P450 Enzymes to Form Hydroxyeicosatetraenoic and Epoxyeicosatrienoic Acid Ethanolamides, pp 590-597 (2007).
9. Campbell W, Gebremedhin D, Pratt P F, Harder D R., Identification of epoxyeicosatrienoic acids as endothelium-derived hyperpolarizing factors. Circulation Research 78:415-423 (1996).
10. Inceoglu B, Kara R, Schmelzer, Christophe Morisseau, Steve L. Jinks, Bruce D. Hammock. Soluble epoxide hydrolase inhibition reveals novel biological functions of epoxyeicosatrienoic acids (EETs). Prostaglandins & other Lipid Mediators in press (2006b),
11. Schmelzer K, Kubala L, Newman J W, Kim I H, Eiserich J P, Hammock B D., Soluble epoxide hydrolase is a therapeutic target for acute inflammation. Proc Natl Acad Sci USA 102:9772-9777 (2005).
12. Inceoglu B, Steven L. Jinks, Kara R. Schmelzer, Troy Waite, In Hae Kim, Bruce D. Hammock, Inhibition of soluble epoxide hydrolase reduces LPS-induced thermal hyperalgesia and mechanical allodynia in a rat model of inflammatory pain. Life Sciences 79 2311-2319 (2006),
13. Schmelzer K. Inceoglu B, Kubala L, Kim I H, Jinks S L, Eiserich J P, Hammock B D., Enhancement of aminoception by coadministration of nonsteroidal anti-inflammatory drugs and soluble epoxide hydrolase inhibitors. Proc Natl Acad Sci USA September 12; ( ): 103:13646-13651 (2006).
14. Ramwell P W, J. E. Shaw and R. Jessup Spontaneous and evoked release of prostaglandins from frog spinal cord. Am J Physiol 211:998-1004. (1966).
15. Malmberg A B, Yaksh, T. L., Hyperalgesia mediated by spinal glutamate or substance P receptor blocked by spinal cyclooxygenase inhibition. Science 257:1276-1279. (1992).
16. Ferreira S H, Lorenzetti B B and Correa F M A, Central and peripheral antialgesic action of aspirin-like drugs. European Journal of Pharmacology 53:39-48 (1978).
17. Aley K O and Levine J D, Rapid onset pain induced by intravenous streptozotocin in the rat. The Journal of Pain 2:146-0.150 (2001).
18. Papadopoulos V, Baraldi M, Guilarte T R, Knudsen T B, Lacapere J-J, Lindemann P, Norenberg M D, Nutt D, Weizman A. Zhang M-R and Gavish M, Translocator protein (18 kDa): new nomenclature for the peripheral-type benzodiazepine receptor based on is structure and molecular function. Trends in Pharmacological Sciences 27:402-409 (2006).
19. Le Fur G, M. L. Perrier, N. Vaucher, F. Imbault. A. Flamier, J. Benavides A U, C. Renault, M. C. Dubroeucq and Gueremy aC, Peripheral benzodiazepine binding sites: effect of PK11195, I-(2-Chlorophenyl)-N-Methyl-N-(1-Methylpropyl)-3-Isoquinolinecarboxamide I. In vitro studies. Life Sciences, 32:1839-1847 (1983).
20. Papadopoulos V, Amri, H., Boujrad, N., Cascio, C., Culty, M., Garnier, M., Hardwick, M., Li, H., Niche, B., Brown, A. S., Peripheral benzodiazepine receptor in cholesterol transport and steroidogenesis. Steroids 62:21-28 (1997).
21. Papadopoulos V L, Brown, R. C. Han, Z. Yao, Z. X., Peripheral-type benzodiazepine receptor in neurosteroid biosynthesis, neuropathology and neurological disorders. Neuroscience 138:749-756 (2006).
22, Li H, Degenhardt B, Tobin D, Yao Z-x, Tasken K and Papadopoulos V. Identification, Localization, and Function in Steroidogenesis of PAP7: A Peripheral-Type Benzodiazepine Receptor- and PKA (RI{alpha})-Associated Protein, pp 2211-2228 (2001).
23. Papadopoulos V, Liu J and Culty M, Is there a mitochondrial signaling complex facilitating cholesterol import? Molecular and Cellular Endocrinology 265-266:59-64 (2007).
24. Bressana E, Roseli C. Fargesa, Pascual Ferrarab, Carlos R. Tonussi, Comparison of two PBR ligands with classical antiinflammatory drugs in LPS-induced arthritis in rats. Life Sciences 72:2591-2601 (2003).
25. da Silva M, Farges R C, Frode T S, Involvement of steroids in anti-inflammatory effects of PK11195 in a murine model of pleurisy. Mediators of inflammation 13:93-103 (2004).
26. Van Voorhis B J, Dunn, M. S., Falck, J. R., Bhatt, R. K., VanRollins, M., Snyder, G. D., Metabolism of arachidonic acid to epoxyeicosatrienoic acids by human granulosa cells may mediate steroidogenesis J Clin Endocrinol Metab 76:1555-1559 (1993).
27. Nishimura M, Hirai A, Omura M, Tamura Y and Yoshida S, Arachidonic acid metabolites by cytochrome P-450 dependent monooxygenase pathway in bovine adrenal fasciculata cells. Prostaglandins 38:413-430 $(1)_{89}$).
28. Lin T, Mechanism of action of gonadotropin-releasing hormone stimulated Leydig cell steroidogenesis III. The role of arachidonic acid and calcium/phospholipid dependent protein kinase. Life Sciences 36:1255-1264 (1985).
29. Dix C, J., A D Habberfield, M H Sullivan, and B A Cooke, Inhibition of steroid production in Leydig cells by nonsteroidal anti-inflammatory and related compounds: evidence for the involvement of lipoxygenase products in steroidogenesis. Biochem J 219:529-537, (1984).
30. Wang X, Shen, Chwan-Li, Dyson, Matthew T., Yin, Xianling, Schiffer, Randolph B., Grammas, Paula, Stocco, Douglas M., The involvement of epoxygenase metabolites of arachidonic acid in cAMP-stimulated steroidogenesis and steroidogenic acute regulatory protein gene expression, pp 871-878 (2006),
31. Miller W L, Steroidogenic acute regulatory protein (StAR), a novel mitochondrial cholesterol transporter. Biochimica et Biophysica Acta (BBA)—Molecular and Cell Biology of Lipids 1771:663-676 (2007).
32. Poisbeau P, Patte-Mensah C, Keller A F, Barrot M, Breton J-D, Luis-Delgado O E, Freund-Mercier M J, Mensah-Nyagan A G and Schlichter R, Inflammatory Pain Upregulates Spinal Inhibition via Endogenous Neurosteroid Production, pp 11768-11776 (2005).
33. Taiwo Y O, Bjerknes L K, Goetzl E J and Levine J D, Mediation of primary afferent peripheral hyperalgesia by the cAMP second, messenger system. Neuroscience 32:577-580 (1989).
34. Hucho T and Levine J D, Signaling Pathways in Sensitization: Toward a Nociceptor Cell Biology, Neuron 55:365-376 (2007).

35. Song X-J, Wang Z-B, Gan Q and Walters E T, cAMP and cGMP Contribute to Sensory Neuron Hyperexcitability and Hyperalgesia in Rats With Dorsal Root Ganglia Compression, pp 479-492 (2006).
36. Wellmam W and Schwabe U, Effects of prostaglandins E1, E2 and F2[alpha] on cyclic AMP levels in brain in vivo. Brain Research 59:371-378 (1973).
37. Taiwo Y O and Levine J D, Further confirmation of the role of adenyl cyclase and of cAMP-dependent protein kinase in primary afferent hyperalgesia. Neuroscience 44:131-135 (1991).
38. Stocco D M, Wang X, Jo Y and Manna P R, Multiple Signaling Pathways Regulating Steroidogenesis and Steroidogenic Acute Regulatory Protein Expression: More Complicated than We Thought, pp 2647-2659 (2005).
39. Manna P R, Chandrala S P, Jo Y and Stocco D M, cAMP-independent signaling regulates steroidogenesis in mouse Leydig cells in the absence of StAR phosphorylation, pp 81-95 (2006).
40. Bodor J, Spetz A-L, Strominger J L and Habener J F, cAMP inducibility of transcriptional repressor ICER in developing and mature human T lymphocytes, pp 3536-3541 (1996).
41. Inceoglu B, Jinks S L, Ulu A, Hegedus C M, Georgi K, Schmelzer K R, Wagner K, Jones P D, Morisseau C and Hammock B D, Soluble epoxide hydrolase and epoxyeicosatrienoic acids modulate two distinct analgesic pathways. *Proc Natl Acad Sci USA*, in press.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of relieving neuropathic pain in a subject in need thereof, said method comprising administering to said subject an effective amount of an agent or agents selected from the group consisting of a cis-epoxyeicosantrienoic acid ("EET"), an inhibitor of soluble epoxide hydrolase ("sEH"), and a combination of an EET and an inhibitor of sEH, thereby relieving said neuropathic pain in said subject.

2. A method of claim 1, wherein the agent is an EET.

3. A method of claim 1, wherein the EET is selected from the group consisting of 14,15-EET, 8,9-EET, 11,12-EET or 5,6-EET.

4. A method of claim 1, wherein the EET is synthetic or an EET analog.

5. A method of claim 1, wherein the agent is an inhibitor of sEH.

6. A method of claim 1, wherein the agent is administered orally.

7. A method of claim 1, wherein the agent is administered intravenously.

8. A method of claim 1, wherein the agent is administered intrathecally.

9. A method of claim 1, wherein the neuropathic pain is central neuropathic pain.

10. A method of claim 1, wherein the neuropathic pain is peripheral neuropathic pain.

11. A method of claim 1, wherein the neuropathic pain is selected from the group consisting of post-herpetic neuralgia, trigeminal neuralgia, focal peripheral nerve injury, and anesthesia dolorosa, central pain due to stroke or mass lesion, spinal cord injury, or multiple sclerosis, and peripheral neuropathy due to diabetes, HIV, or chemotherapy.

12. A method of claim 1, wherein the subject is experiencing neuropathic pain at the time of administration.

13. A method of claim 1, wherein the inhibitor of sEH comprises a pharmacophore comprising a urea, a carbamate, or an amide.

14. A method of claim 1, wherein the inhibitor of sEH comprises an $IC_{50}$ of less than about 500 μM 15. A method of claim 1, wherein the inhibitor of sEH comprises an $IC_{50}$ of less than about 1 μM

* * * * *